(12) United States Patent
Wenzel et al.

(10) Patent No.: US 9,464,294 B2
(45) Date of Patent: Oct. 11, 2016

(54) REGULATION OF INDUCIBLE PROMOTERS

(76) Inventors: Marian Wenzel, Neidlingen (DE); Josef Altenbuchner, Nufringen (DE); Christoph Kiziak, Visp (CH)

(*) Notice: Subject to any disclaimer, the term of this patent is extended or adjusted under 35 U.S.C. 154(b) by 0 days.

(21) Appl. No.: 13/813,035

(22) PCT Filed: Jul. 27, 2011

(86) PCT No.: PCT/EP2011/062921
§ 371 (c)(1),
(2), (4) Date: Mar. 27, 2013

(87) PCT Pub. No.: WO2012/013710
PCT Pub. Date: Feb. 2, 2012

(65) Prior Publication Data
US 2013/0203114 A1 Aug. 8, 2013

(30) Foreign Application Priority Data

Jul. 29, 2010 (EP) .................. 10171252
Apr. 14, 2011 (EP) .................. 11162420

(51) Int. Cl.
| | | |
|---|---|---|
| C12P 21/02 | (2006.01) |
| C12N 15/75 | (2006.01) |
| C12N 15/63 | (2006.01) |
| C12N 15/70 | (2006.01) |
| C12N 1/21 | (2006.01) |
| C12N 15/09 | (2006.01) |
| C12N 15/67 | (2006.01) |

(52) U.S. Cl.
CPC .......... *C12N 15/635* (2013.01); *C12N 15/63* (2013.01); *C12N 15/70* (2013.01); *C12N 15/75* (2013.01)

(58) Field of Classification Search
None
See application file for complete search history.

(56) References Cited

U.S. PATENT DOCUMENTS

2012/0196323 A1* 8/2012 Wenzel et al. ............... 435/69.1
2012/0202246 A1* 8/2012 Sun et al. .................... 435/69.1

OTHER PUBLICATIONS

Gosset, "Improvement of *Escherichia coli* production strains by modification of the phosphoenolpyruvate:sugar phsophortransferase system" 4 MIcrobial Cell Factories 14 (1-11) (2005).*
Vary et al., "Bacillus megaterium—from simple soil bacterium to industrial protein production host" 76 Applied Microbiology and Biotechnology 957-967 (2007).*
Comus et al., "Unraveling the evolutionary history of the phosphoryl-transfer chain of the phosphoenolpyruvate:phosphotransferase system through phylogenetic analyses and genome context" 8 BMC Evolutionary Biology 147 (1-18) (2008).*
Tianki Sun. "Regulation des Mannose-Operons in Bacillus subtilis, Dissertation zur Erlangung der Wurde eines Doktors in Naturwissenschaften," Internet citation. Date: Apr. 16, 2010. pp. I-VI, XP002604428.

Sun Tianqi et al. "Characterization of a mannose utilization system in Bacillus subtilis," Journal of Bacteriology, American Society for Microbiology, Washington, DC. vol. 192, No. 8. Date: Apr. 1, 2010.
Tobisch Steffen et al., "Regulation of the lic operon of Bacillus subtilis and characterization of potential phosphorylation sites of the LicR regulator protein by site-directed mutagenesis," Journal of Bacteriology. vol. 181, No. 16, pp. 4995-5003, XP002614551, ISSN: 0021-9193. Date: Aug. 1999.
Wilms Burkhard et al., "High-cell-density fermentation for production of L—N-carbamoylase using an expression system based on the *Esherichia coli* rhaBAD promoter," Bioltechnology and Bioengineering. vol. 73, No. 2, pp. 95-103, XP002228440, ISSN: 0006-3592. Date: Apr. 20, 2001.
Gorke Boris et al., "Carbon catabolite repression in bacteria: many ways to make the most out of nutrients," Nature Reviews. Microbiology. vol. 6, No. 8, pp. 613-624, XP009142600, ISSN: 1740-1534. Date: Aug. 2008.
Deutscher et al., "The mechanisms of carbon catabolite repression in bacteria," Current Opinion in Microbiology, Current Biology Ltd., GB. vol. 11, No. 2, pp. 87-93, XP022616728, ISSN: 1369-5274. Date: Apr. 1, 2008.
Abranches Jacqueline et al., "Characterization of *Streptococcus mutans* strains deficient in EIIAB Man of the sugar phosphotransferase system," Applied and Environmental Microbiology, American Society for Microbiology, US. vol. 69, No. 8, pp. 4760-4769, XP002558891, ISSN: 0099-2240. Date: Aug. 1, 2003.
Tianki, Sun. "Regulation des Mannose-Operons in Bacillus subtilis, Dissertation zur Erlangung der Wurde eines Doctors in Naturwissenshaften." Internet citation, Apr. 16, 2010, pp. I-VI, XP002604428. Retrieved from Internet on Nov. 10, 2010: www.elib.uni-stuttgart.de/opus/volltexte/2010/5249/pdf/Regulation_des_Mannose_Operons.pdf.
Sun, Tianqui et al. "Characterization of a mannose utilization system in Bacillus subtilis." Journal of Bacteriology. American Society for Microbiology. Washington, DC. vol. 192, No. 8. Apr. 1, 2010. pp. 2128-2139, XP002604427, ISSN: 0021-9193, DOI: DOI: 10.1128/JB.01673-09.
Tobisch, Steffen et al. "Regulation of the lic operon of Bacillus subtilis and characterization of potential phosphorylation sites of the LicR regulator protein by site-directed mutagenesis." Journal of Bacteriology. vol. 181, No. 16. Aug. 1999. pp. 4995-5003, XP002614551, ISSN: 0021-9193.
Wilms, Burkhard et al. "High-cell-density fermentation for production of L—N-carbamoylase using an expression system based on the *Escherichia coli* rhaBAD promoter." Biotechnology and Bioengeneering. vol. 73, No. 2. Apr. 20, 2001. pp. 95-103, XP002228440, ISSN: 0006-3592.
Gorke, Boris et al. "Carbon catabolite repression in bacteria: many ways to make the most out of nutrients." Nature Reviews. Microbiology. Aug. 2009. LNKD-PUBMED: 18628769. vol. 6, No. 8. pp. 613-624. XP009142600. ISN: 1740-1534.

(Continued)

*Primary Examiner* — Nancy J Leith
(74) *Attorney, Agent, or Firm* — Steven M. Shape

(57) ABSTRACT

The present invention relates to the production of heterologous polypeptides in a recombinant bacterial host cell, wherein the bacterial host cell is rendered inable to deactivate the promoter controlling the expression of the heterologous polypeptide in the absence of an inducer.

13 Claims, 9 Drawing Sheets

(56) References Cited

OTHER PUBLICATIONS

Deutscher, et al. "The mechanisms of carbon catabolite repression in bacteria." Current Opinion in Microbiology, Current Biology Ltd. GB. vol. 11, No. 2. Apr. 1, 2008. pp. 87-93, XP022616728, ISSN: 1369-5274, DOI: DOI:10-1016/J.MIB.2008.02.007.

Abranches, Jacqueline et al. "Characterization of *Streptococcus mutans* strains deficient in EIIAB Man of the sugar phosphotransferase system." Applied and Environmental Microbiology, American Society for Microbiology, US. vol. 69, No. 8. Aug. 1, 2003. pp. 4760-4769, XP002558891, ISSN: 0099-2240, DOI: DOI:10.1128/AEM.69.8.4760-4769.2003.

\* cited by examiner

Operon-structure (Mannose)

Mannose-Catabolism

Nucleic acid sequence with Sequence Nos. 1 and 2:

```
TTTTATCTCA TTTGGATTAT TAAAAGCAGG GATTATTCCT TGCTTTTTTT
           manR                                    -35
GTTATAGGGA AAAATGCCTT TATTACCGGA ACCTATGGTA AAAAAAGCGA
                         -10         +1  BglII
TTTTAATGAG CTGATTTCGG TATACAGTTG AGACAAGATC TTATTATTCA
     XbaI            AflII                NdeI
CACTTTCTAG AAATAATTTT CTTAAGAAGG AGATATACAT ATGACACATG
                                                  Lysa_Bs
```

Fig. 3

Nucleic acid sequence with Sequence Nos. 3, 4 and 5:

```
    pSUN291              pSUN384.1           pSUN385.2
TGAATTTCTG CTGAATATAC ATTACATAGC AAACTCAAAG AGTATAAAAA pSUN386.9 HindIII           -35
TCGCTTTTTT CCGGAAGCTT CGGTAAAAAA CGAAACTTTT GTCTCTATGA PsiI  -10        +1
TTTTGTTTTA TAATGTAAAC GGTTTCTTAT ATAGTATACT TATACTATCA
        >>...CRE..>>

AflII                 NdeI
ATTTGCTCAA GTAGATACTG ACAGGCTTAA GAAGGAGATA TACATATGAC
                                                   >lacZ
```

Fig. 4

Nucleic acid sequence with part of Sequence Nos. 4 and 5:

```
     HindIII                  -35
TTTTTCCGGA AGCTTCGGTA AAAACGAAA CTTTTGTCTC TATGATTTTG
    -10    CRE    +1
TTTTA TAATTT TAAACGGTTT CTTATATAGT ATACTTATAC TATCAATTTG CTCAAGTAGA TACTGACAGG AAGGATAGAA AAACAGATGG AATACATAAA
                                          manR
```

Fig. 5

Nucleic acid sequence with Sequence Nos. 1 and 2:

```
                 ┌─────────→ pSUN284.1
         NruI
TCAGCAATCG CGATTGCCAC ATTAAAGGAG CCGCTTGAAT GGGGAAATGA AAAAGTTTCG CTCGTTTTTA
────────────────────────────────────── manR ───────────────────────────────────

TGCTGGCTGT CAAACACGAG GATCAAACTA TGACAAAGCA GCTGTTTAGC GAGCTTTCAT ATCTTAGCGA
────────────────────────────────────── manR ───────────────────────────────────
                                                              ┌────────→ pSUN289.3
GCAGCCGGCC TTCGTCCAGA AGCTGACGAA AGAAACCAAT GTCATGACAT GTCATGACAT TTTTATCTCA
────────────────────────────────────── manR ───────────────────────────────────
                          ┌──────→ pSUN298.1       ┌──────────→ pSUN290
     IRI                      IRI                        ┌──→ pSUN380.1 ┌
TTTGGATTAT TAAAAGCAGG GATTATTCCT TGCTTTTTTT GTTATAGGGA AAAATGCCTT TATTACCGGA
- - manR - - - - - ►                  IRII
─→pSUN381.1 ┌──────→ pSUN297.5
  ┌              -35                       -10            +1 BglII
ACCTATGGTA AAAAAGCCGA TTTTAATGAG CTGATTTCGG TATACAGTTG AGACAAGATC TTATTATTCA
    IRII
     XbaI              AflII           NdeI
CACTTTCTAG AAATAATTTT CTTAAGAAGG AGATATACAT ATGACCATGA
                                                    └──────lacZ →
```

Fig. 8

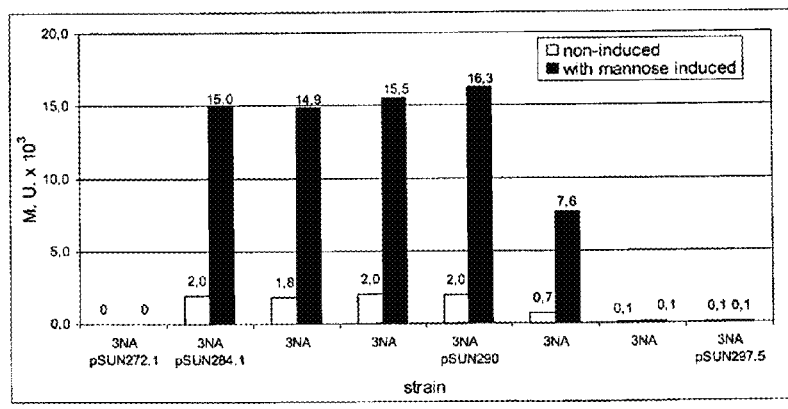

Fig. 9

Fed-batch fermentation of *B. subtilis* TQ356 / pMW166.1. Cell dry weight (X, black circles), total produced amount of eGFP ($P_{eGFP}$, black squares) and product yield (P/X, black triangle) are plotted over the fermentation time. The beginning of the fed-batch phase is indicated by a vertical line.

SDS-PAGE of cell samples taken from the fermentation with B. subtilis TQ356 / pMW168.1. Lanes 1-8, M: Roti®-Mark STANDARD protein molecular weight marker; 1: after 12.5 h (batch); 2: after 20.5 h (batch); 3: after 36 h (13,5 h fed-batch); 4: after 41 h (18,5 h fed-batch); 5: after 44 h (21,5 h fed-batch); 6: after 46 h (23,5 h fed-batch, end of process); 7: after 46 h, unsoluble fraction; 8: after 46 h, culture supernatant.

REGULATION OF INDUCIBLE PROMOTERS

The present invention relates to the production of heterologous polypeptides in a recombinant bacterial host cell. In particular, the present invention relates to the regulation of the expression of a heterologous nucleic acid sequence encoding for the polypeptide by the use of a promoter inducible by a specific substrate (inducer). Most particularly, the present invention relates to the regulation of the expression of heterologous polypeptide in a bacterial host cell wherein the bacterial host cell is rendered inable to deactivate the promoter controlling the expression of the heterologous polypeptide in the absence of inducer.

BACKGROUND OF THE INVENTION

An important aspect in heterologous polypeptide production in recombinant microorganism is the selection of the promoter used for controlling the expression of the heterologous nucleic acid sequences which encodes the target polypeptide.

A suitable promoter should be strong. That is, produce the respective mRNA in a high rate allowing production of the polypeptide in high amount. Further, the promoter should be readily to be regulated and start the production of the heterologous polypeptide only upon induction.

However, there is the problem that typically the inducing substrate is a nutrient for the microorganism and is consumed by the microorganism. However, when the medium used for cultivating the microorganism runs out of the inducing substrate, the microorganism deactivates the promoter and, thus, expression of the target polypeptide stops. For avoiding unwanted stop of gene expression, the inducer must be added in high amounts and/or continuously supplemented. The need of high amounts of inducer raises the costs of the fermentation process. Further, use of efficient promoters which, however, require expensive inducers is restricted.

Consequently, for the recombinant polypeptide production host cells are desired wherein the activity of the promoter controlling the expression of the heterologous polypeptide is independent from the presence of the inducer but wherein expression of the heterologous polypeptide can be nevertheless tightly regulated.

WO 2006/133210 A2 relates to a method for producing recombinant peptides in a bacterial host cell utilizing a mannitol, arabitol, glucitol or glycerol-inducible promoter, wherein the bacterial host cell has been rendered incapable of degrading or metabolizing the inducer. According to said method a gene or genes encoding for enzymes required for metabolizing the inducer is genetically altered or deleted in the genome so that the cell cannot express, from its genome, a functional enzyme necessary for metabolizing or degrading the inducer. In order to ensure uptake of the inducer genes related to the transport of the inducer into the cell, are unaffected. This method, however, requires nevertheless addition of inducer for catalyzing activation of the respective promoter controlling expression of the target polypeptide. Further, accumulation of inducer in the cell can negatively affect development of the cell.

Many bacteria are able to utilize different carbon sources. If provided with a mixture of carbon sources the carbon source that allows the most rapid growth (primary carbon source) is selected. Simultaneously the functions involved in the utilization of secondary carbon sources are repressed by a phenomenon called carbon catabolite repression (CCR).

Besides CCR the specific catabolic genes involved in the utilization of a less preferred secondary carbon source are only expressed in the presence of said secondary carbon source. Consequently, expression of genes involved in catabolismn of a secondary carbon source depends on the presence of said secondary carbon source (induction) and the absence of a primary carbon source (catabolite repression).

The publication of Tianqui Sun et al "Characterization of a mannose utilization system in *bacillus subtilis*", Journal of Bacteriology, American Society for Microbiology, vol. 192, no 8, Apr. 1, 2010, pages 2128 bis 2139 relates to the identification of the mannose operon and its genes as well as of the promoters PmanP and PmanR regulated by mannose. It is reported that the metabolism of mannose is subject to the phosphoenolpyruvate: carbohydrate phosphotransferase system and that the mannose operon is further subject to carbon catabolite repression. For the characterization and identification of function of the individual genes knockout-mutants were prepared lacking the respective genes and, consequently, lacking the respective proteins encoded by said genes. It was found that deletion of the mannose transporter gene manP resulted in constitutive expression from both the promoters PmanP and PmanR, indicating that the mannose transporter ManP has a negative effect on regulation of the mannose operon and the manR gene encoding for the mannose specific transcriptional regulator ManR.

Tobisch et al. "Regulation of the lic operon of *Bacillus subtilis* and characterization of potential phosphorylation sites of the LiR regulator protein by site-directed mutangenesis" in Journal of Bacteriology, vol. 181, no. 16, Aug. 19, 1999, pages 4995-5003 reports that exchange of the phosphoryl group binding amino acid in the EIIA domain of the regulator LicR by another amino acid results in activity of the mutant regulator LicR in the absence of inducing substrate.

Görke et al. "Carbon catabolite repression in bacteria: Many ways to make the most out of nutrients" in Nature Reviews. Microbiology, vol. 6, no. 8, August 2008, pages 613-624 relates to *Streptococcus* mutant strains deficient in mannose transporter EIIAB and the influence on phosphoenolpyruvate: carbohydrate phosphotransferase system. It is shown that the mannose transporter EIIAB is not limited to the phosphorylation of mannose only but likewise phosphorylates glucose, fructose and 2-deoxyglucose. Further, it is shown that even in the absence of the mannose transporter EIIAB mannose can be taken up via the fructose specific transporter $EII^{FRU}$.

Deutscher et al "The mechanisms of carbon catabolite repression in bacteria" (Current Opinion in Microbiology, Current Biology LTD, GB, vol. 11, no. 2, Apr. 1, 2008, pages 87-93) gives a general overview of mechanism of carbon catabolite repression in different bacteria, for example *E. coli* and *B. subtilis*.

SUMMARY OF THE INVENTION

The present invention makes use of these regulation mechanisms of carbon catabolism by providing a bacterial host cell wherein the promoter regulating the expression of the genes involved in the metabolism of a secondary carbon source is not deactivated in the absence of its corresponding carbon source, and wherein the promoter is solely under control of carbon catabolite repression.

According to the present invention, the promoter used is a promoter which regulates the utilization of a secondary carbon source of the bacterial host cell.

In the presence of a primary carbon source the promoter is repressed by CCR. When the medium used to cultivate the recombinant bacterial host cell runs out of primary carbon source or the concentration of primary carbon source decreases below a level required for CCR, CCR of the promoter is rendered inoperative and the promoter automatically starts expression of the genes controlled by said promoter.

The present invention provides for a recombinant bacterial host cell wherein the recombinant bacterial host cell is capable of utilizing more than one carbon source, wherein carbon catabolism of these carbon sources of the bacterial host cell is subjected to the phosphoenolpyruvate: carbohydrate phosphotransferase system (PTS) and CCR, wherein the bacterial host cell is genetically altered to prevent deactivation of the transcriptional regulator protein of a carbon source inducible promoter in the absence of said secondary carbon source, but is under control of CCR, wherein the carbon source is a secondary carbon source for the bacterial host cell.

According to a further aspect of the present invention the recombinant bacterial host cell of the present invention is transformed with a vector comprising a heterologous nucleic acid sequence encoding a polypeptide operably linked to a promoter inducible by a secondary carbon source, wherein the promoter of the vector is controlled by the transcriptional regulator protein for which the bacterial host cell has been genetically altered to be incapable of deactivation in absence of the specific corresponding carbon source.

Furthermore, the present invention provides for a process for preparing heterologous polypeptides by culturing the recombinant bacterial host cell of the present invention transformed with a vector which comprises the nucleic acid sequence encoding for the polypeptide.

Further, the present invention relates to the use of a recombinant bacterial host cell according to the present invention in the production of heterologous polypeptides.

According to a particular aspect the present invention relates to an induction regime of gene expression requiring a reduced amount of inducer and, in particular, no inducer et all. According to a further particular aspect, the present invention relates to a bacterial expression system suitable in high cell density fermentation.

In particular the present invention provides for a method for producing a heterologous polypeptide in a recombinant bacterial host cell, wherein a recombinant bacterial host cell is used, whose catabolism of carbon sources is under the control of carbon catabolite repression and phosphoenolpyruvate: carbohydrate phosphotransferase system and which is genetically altered such, that it is incapable to deactivate the transcriptional regulator protein specific for a promoter inducible by a secondary carbon source in the absence of the inducing secondary carbon source, and which comprises a vector with a heterologous nucleic acid sequence encoding a polypeptide operably linked to a promoter, which is inducible by the secondary carbon source and is regulated by the transcriptional regulator protein, said method comprising the steps of growing the bacterial host cell in a cell culture medium, that does not comprise the inducing carbon source but a different carbon source, inducing the expression of said polypeptide by the different carbon source at a time, when the concentration of the different carbon source decreases under a level necessary for carbon catabolite repression, and recovering the polypeptide from the cells or from the cell culture.

Further the present invention provides for recombinant bacterial host cells suitable for carrying out the method of the present invention.

For example the present invention relates to a recombinant bacterial host cell whose catabolism of carbon sources is under control of carbon catabolite repression and phosphoenolpyruvate: carbohydrate phosphotransferase system, and which is genetically altered such, that it is incapable to deactivate the transcriptional regulator protein specific for a promoter inducible by a secondary carbon source in the absence of the inducing secondary carbon source by deleting in the genome of the bacterial host cell the gene which encodes for a phosphoryl group transferring enzyme EII specific for the transcriptional regulator protein, and which comprises a vector with a heterologous nucleic acid sequence encoding a polypeptide operably linked to a promoter, which is regulated by the transcriptional regulator protein for which the bacterial host cell is genetically altered to be incapable of deactivation, and wherein into the vector is integrated the gene encoding for the specific transcriptional regulator protein.

Further, the present invention relates to a recombinant bacterial host cell whose catabolism of carbon sources is under control of carbon catabolite repression and phosphoenolpyruvate: carbohydrate phosphotransferase system, and which is genetically altered such, that it is incapable to deactivate the transcriptional regulator protein specific for a promoter inducible by a secondary carbon source in the absence of the inducing secondary carbon source by genetically altering in the genome of the bacterial host cell the gene encoding for the transcriptional regulator protein so that the transcriptional regulator protein expressed by said gene is incapable of binding a phosphoryl group transferred by enzyme EII, specific for said transcriptional regulator protein, and which comprises a vector with a heterologous nucleic acid sequence encoding a polypeptide operably linked to a promoter regulated by the transcriptional regulator protein for which the bacterial host cell is genetically altered to be incapable of deactivation, and wherein into the vector is additionally integrated the manipulated gene encoding for the transcriptional regulator protein incapable of binding a phosphoryl group transferred by the corresponding enzyme EII.

According to yet a further aspect the present invention relates to a method for the production of a heterologous polypeptide by culturing a recombinant bacterial host cell, wherein a recombinant bacterial host cell is used whose catabolism of carbon sources is under control of carbon catabolite repression and phosphoenolpyruvate: carbohydrate phosphotransferase system, and which is genetically altered such, that it is incapable of metabolizing the inducing carbon source of a carbon source inducible promoter, wherein the inducing carbon source is a secondary carbon source for the bacterial host cell, and which comprises a vector with the promoter inducible by said secondary carbon source and a heterologous nucleic acid sequence encoding a polypeptide operably linked to the promoter, wherein the process is a fed-batch process, wherein after the batch phase induction is started by adding a first portion of the inducing secondary carbon source and, simultaneously, feeding of a second portion is started.

Other objects and advantages will become apparent to those skilled in the art from review of the following detailed description with reference to the accompanying illustrative figures and the attached claims.

According to the embodiment referred to above induction of the expression of a target polypeptide is independent of the presence of an inducing carbon source for the promoter. Thus, this embodiment is particularly advantageous in that no inducing carbon source is required.

However, it would be also helpful from an economical point of view, if the amount of carbon source necessary for inducing the promoter can be reduced.

Thus, according to an alternative solution the present invention relates to a method for producing a target polypeptide by expression of a nucleotide sequence encoding for said target polypeptide, wherein the expression is under control of a carbon source inducible promoter, wherein the process of catabolism of the inducing carbon source by the bacterial host cell, which shall be transformed with a vector carrying the promoter and the nucleotide sequence of a target polypeptide, is interrupted or at least retarded.

According to the present invention this alternative is achieved by eliminating or genetically altering in the genome of the bacterial host cell the nucleotide sequence encoding for the inducing carbon source specific isomerase, which converts the inducing carbon source, once transported into the cell, to fructose-6-phosphate. Isomerisation to fructose-6-phosphate is the first step in catabolism of a carbon source once the carbon source has been transported into the cell. Interrupting or retarding the isomerisation of the carbon source means that the carbon source is available for induction for a prolonged period of time. Consequently, the amount of inducing carbon source can be reduced.

According to an example this alternative relates to a mannose inducible promoter, and a bacterial host cell for such promoter wherein in the genome of the bacterial host cell the gene encoding the mannose-6-phosphate isomerase, also referred to ManA, has been eliminated or genetically altered so that isomerisation of mannose, once transported into the cell, is not possible or at least retarded.

BRIEF DESCRIPTION OF THE FIGURES

It is shown in

FIG. 3 schematically illustrates the structure of the ManR activator protein with the various domains and potential phosphorylation sites showing a nucleic acid sequence comprising sequence numbers 1 and 2;

FIG. 4 shows the nucleic acid sequence of the promoter region of *B. subtilis* comprising manR promoter and sequence numbers 3, 4 and 5;

FIG. 5 shows a nucleic acid sequence with part of sequence numbers 4 and 5 with the cre-sequence and the transcription initiation site G at bp+1;

FIG. 8 shows the nucleic acid sequence form *B. subtilis* used in the promoter-probe vector pSUN272.1 for studying inducibility and catabolite repression of the manP promoter by mannose and glucose and determination of the ManR binding site comprising sequence numbers 1 and 2;

FIG. 9 the β-galactosidase activities of *B. subtilis* 3NA containing the plasmid pSUN 284.1 as well as further plasmids containing fragments of different lengths of the nucleic acid sequence shown in FIG. 5;

DETAILED DESCRIPTION OF THE INVENTION

Figure 1:
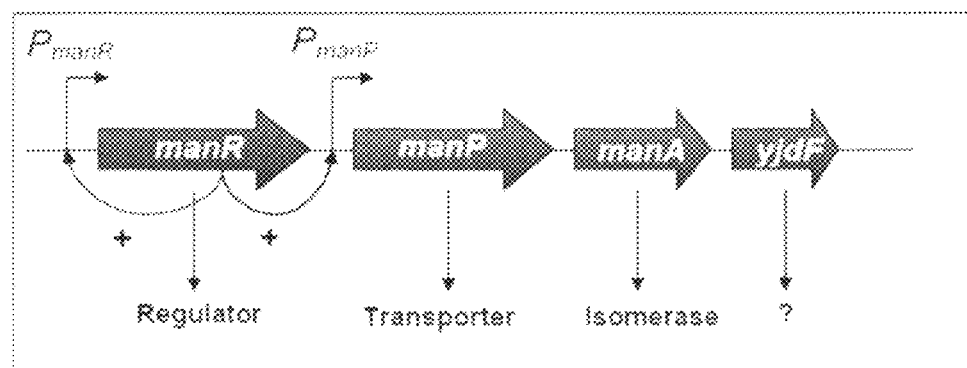
FIG. 1 schematically the structure of the mannose operon with the arrangement and orientation of the respective genes and the promoters and activation thereof by ManR indicated by arrows.

As used herein, the following definitions are supplied in order to facilitate the understanding of the present invention.

"Enzyme EII", "EII" or "transporter" refer to a carbon source specific permease of the phosphoenolpyruvate: carbohydrate phosphotransferase system (PTS), which catalyzes the transport and concomitant phosphorylation of the carbon source.

The PTS comprises a variety of EIIs, each specific for a carbon source, for example a sugar.

EIIs are complexes usually consisting of three domains A, B and C, and sometimes a forth domain D, wherein EIIA and EIIB participates in phosphorylation of the corresponding carbon source, and the membrane bound EIIC (END, if present) mediates passage of the specific carbon source into the cell.

In the absence of the specific carbon source the corresponding EiIA and, in some cases, EIIB deactivate the respective carbon source specific transcriptional regulator protein by transfer of phosphoryl groups to corresponding phosphorylation sites present in the transcriptional regulator protein, referred to—depending on the phosphorylating EII—EIIA and EIIB domain, respectively.

"Transcriptional regulator protein" or "regulator" positively regulates (i.e. activates) the catabolic operon(s) of the specific carbon source. The transcriptional regulator proteins usually contain two conserved regulatory domains that can be phosphorylated (PTS regulatory domains, PRDs). Further, some transcriptional regulator proteins in addition contain further phosphorylation sites referred to EIIA and EIIB. Depending on the transcriptional regulator protein the transcriptional regulator protein is deactivated by phosphoryl group transfer from enzyme II to one or more of the above phosphoryl binding sites in the EIIA and EIIB and/or PRDI domain, and activated by phosphoryl group transfer from histidine protein (HPr) to the PRDII domain. The various carbon source specific transcriptional regulator proteins of the PTS can be activators or antiterminators.

"Promoter" as used herein refers to a nucleic acid sequence that regulates expression. A "promoter region" is a regulatory region capable of binding RNA polymerase in a cell and initiating transcription of a downstream (3'-direction) coding sequence. Within the promoter region will be found protein binding domains (consensus sequences) responsible for the binding of RNA polymerase such as the −35 box and the −10 box (Pribnow box). Further, the promoter region may comprise the transcription start site and binding sites for their specific transcriptional regulator protein.

With "variants" or "variants of a sequence" is meant a nucleic acid sequence that varies from the reference sequence by conservative nucleic acid substitutions, whereby one or more nucleic acids are substituted by another with same characteristics. Variants encompass as well degenerated sequences, sequences with deletions and insertions, as long as such modified sequences exhibit the same function (functionally equivalent) as the reference sequence.

A "vector expressible in a host" or "expression vector" is a polynucleic acid construct, generated recombinantly or synthetically, with a series of specified polynucleic acid elements that permit transcription of particular nucleic acid sequence in a host cell. Typically, this vector includes a transcriptional unit comprising a particular nucleic acid sequence to be transcribed operably linked to a promoter. A vector expressible in a host can be for example an autonomously or self-replicating plasmid, a cosmid, a phage, a virus or a retro-virus.

The terms "transformation", "transformed" or "introducing a nucleic acid into a host cell" denote any process wherein an extracellular nucleic acid like a vector, with or without accompanying material, enters a host cell.

Transformation of appropriate host cells with, for example, an expression vector can be accomplished by well known methods such as microinjection, electroporation, particle bombardement or by chemical methods such as Calcium phosphate-mediated transformation and by natural transformation systems, described, for example, in Maniatise et al., Molecular Cloning A laboratory Manual, Cold Spring Harbor Laboratory (1982) or in Ausubel et al., Current protocols in molecular biology, John Wiley and Sohns (1984).

"Heterologous nucleic acid sequence" or "nucleic acid sequence heterologous to a host" means a nucleic acid sequence which encodes, for example, an expression product such as a polypeptide that is foreign to the host "heterologous expression" or "heterologous product" i.e. a nucleic acid sequence originating from a donor different from the host or a chemically synthesized nucleic acid sequence with encodes, for example, an expression product such as a polypeptide that is foreign the host. In case the host is a particular prokaryotic species, the heterologous nucleic acid sequence is preferably originated from a different genus of family, more preferred from a different order or class, in particular from a different phylum (division) at most particular from a different domain (empire) of organisms.

The heterologous nucleic acid sequence originating from a donor different from the host can be modified, before it is introduced into the host cell, by mutations, insertions, deletions or substitutions of single nucleic acids or a part of the heterologous nucleic acid sequence as long as such modified sequences exhibit the same function (functionally equivalent) as a reference sequence. A heterologous nucleic acid sequence as referred herein encompasses as well nucleic sequences originating from a different domain (empire) of organisms such as from eukaryotes (of eukaryotic origin) such as, for example, human men antibodies which have been used in phage display libraries and of which single nucleic acids or a part of the nucleic acid sequences have been modified according to the "codon usage" of a prokaryotic host.

"Heterologous polypeptide" or "target polypeptide" within the meaning of the present invention can be a heterologous protein of human, mammalian or prokaryotic origin. Other proteins are antigens such as glycoproteins and carbohydrates from microbial pathogens, both viral and antibacterial, and from tumors. Other heterologous polypeptides are enzymes like chymosin, proteases, polymerases, dehydrogenases, nucleases, glucanases, oxidases, alpha-amylase, oxidoreductases, lipases, amidases, nitril hydratases, esterases or nitrilases.

"Carbon source" refers to a carbon source, typically a carbohydrate, which can be taken up and metabolized by a bacterial cell and is subject to PTS and carbon catabolite repression (CCR), typical examples for carbohydrates are sugars and sugar derivates.

Many bacteria can utilize more than one carbohydrate as a source of carbon and energy. By using specific extracellular enzymes bacteria such as Bacilli are capable of degrading several polysaccharides that are present in large amount in plant biomass. The resulting oligo-, di-, or monosaccharides are transported into the cell and further processed. Usually, the catabolic enzymes involved in the metabolism or degradation of the saccherides are synthesized only when the specific substrate is present in the culture medium and preferred carbon and energy sources are absent. A preferred carbohydrate transport pathway for transporting carbohydrates through the membrane of the cell of bacteria is the PTS.

In the PTS the transport of the carbohydrate through the membrane and subsequent phosphorylation is mediated by an enzyme specific for said carbohydrate referred to enzyme II (EII). Since EII mediates the transport of its corresponding carbon source into the cell EII is also referred to "transporter".

In the presence of a mixture of carbohydrates cells selectively take up the carbon source that provide them with the most energy and growth advantage (primary carbon source). Simultaneously, they repress the various functions involved in the catabolism and uptake of the less preferred carbon sources (secondary carbon source) Typically, a primary carbon source for most bacteria is glucose and depending on the bacterium various other sugars and sugar derivates being used as secondary carbon sources. However, a primary carbon source can also be another compound. E.g. in case of pseudomonads a primary carbon can be an aromatic compound.

Secondary carbon sources include e.g. mannose, lactose and melibiose without being restricted to these.

In the PTS the various catabolic genes involved in the metabolism of specific carbon source are controlled by transcriptional regulator proteins. These transcriptional regulator proteins can act as antiterminators or transcription activator and are only active in the presence of a specific carbon source (inducer). It has been found that EII has a negative (deactivating) regulation effect to its corresponding transcriptional regulator protein by transferring phosphoryl groups to a specific binding site present in the transcriptional regulator protein.

In the absence of a primary carbon source and presence of the promoter specific inducing carbon source the promoter is activated by its corresponding transcriptional regulator protein and genes under control of this promoter are expressed. In the absence of the inducing carbon source the transcriptional regulator protein regulating the promoter is deactivated by phosphoryl group transfer from its EII to the respective binding site on the transcriptional regulator protein, thereby deactivating the promoter and stopping expression of the genes under control of said promoter.

Otherwise, in the presence of a preferred primary carbon source—irrespectively whether or not less preferred secondary carbon sources are present—expression of the catabolic genes of said secondary carbon sources are repressed by CCR.

Generally, the present invention is based on the inhibition of regulation of the carbon source specific transcriptional regulator protein in the absence of said specific carbon source. In particular, the present invention is based on preventing repression or deactivation by phosphoryl group transfer via the corresponding EII to the transcriptional regulator protein.

If repression of a carbon source specific transcriptional regulator protein is prevented, a promoter for which said transcriptional regulator protein is an activator is active irrespective of the presence of a carbon source being an inducer for said promoter. Consequently, no inducing carbon source is necessary for expression of a gene under control of such a promoter and, further, the gene is continuously expressed.

In view of the above the present invention makes use of a promoter inducible by a secondary carbon source wherein the promoter is controlled by PTS on one side and by CCR on the other side.

Accordingly the present invention seeks to prevent deactivation of a carbon source inducible promoter used as promoter in the expression of a target polypeptide by preventing deactivation of the transcriptional regulator protein specific for said promoter.

According to a first approach this goal is achieved by interrupting phosphorylation of the transcriptional regulator protein by its specific EII by rendering at least one binding site of the transcriptional regulator protein for a phosphoryl group transferred by EII unable to bind the phosphoryl group.

To this, in the genome of the bacterial host cell, the gene encoding for the transcriptional regulator protein can be genetically manipulated so that the gene expresses a transcriptional regulator protein which is incapable of binding a phosphoryl group transferred from EII.

According to a second approach phosphorylation is interrupted by deleting, in the genome of the bacterial host cell, the gene encoding for EII, i.e. the enzyme regulating activity of the transcriptional regulator protein.

According to the present invention expression of a heterologous polypeptide is put under control of a promoter which is specific for the transcriptional regulator protein referred to above, for which deactivation by phosphoryl group transfer via EII is prevented by genetical alteration of the bacterial host cell.

The present invention provides for an advantageous system for producing heterologous polypeptides by fermentation of the recombinant bacterial host cell of the present invention transformed with a vector comprising the heterologous nucleic acid encoding for said polypeptide operably linked to a carbon source inducible promoter, wherein the promoter is active even when no inducing carbon source is present in the fermentation medium. Since the promoter controlling the expression of the nucleic acid sequence encoding for the target polypeptide is still under control of carbon catabolite repression no expression takes place in the presence of a primary carbon source such as glucose, but induction is achieved automatically when the system runs out of the primary carbon source (auto-induction). Since activity of the promoter controlling expression of the heterologous polypeptide is independent from the presence of an inducing carbon source, in the fermentation medium induction of expression of the target polypeptide is achieved without the need of an inducing carbon source.

The present invention is advantageous in that the recombinant bacterial host cells can be grown to high cell density in the presence of their primary carbon source, and as soon as a desired cell density is achieved, production of the target polypeptides starts automatically on release of carbon catabolite repression of the promoter controlling expression.

A further advantage of the present invention is that in fed batch fermentation during the batch phase no or nearly no production of the target polypeptide takes place, that is, there is strong catabolite repression.

Suitable bacterial host cells for the present invention are those which can utilize more than one carbon source wherein utilization of the different carbon sources is subject to carbon catabolite repression and wherein the transport of the carbon source through the membrane and phosphorylation thereof is subject to the phosphoenolpyruvate: carbohydrate phosphotransferase system.

Bacterial host cells suitable for the present invention can be Gram-positive or Gram-negative bacteria. Preferred examples are those belonging to the phylum Firmicutes, and, in particular, those belonging to the class Bacilli. Specific examples are those of genus *Bacillus* such as *B. subtilis*, *B. amyloliquifaciens*, *B. licheniformis*, *B. natto*, *B. megaterium*, etc., other preferred examples include i.a. *Streptococcus*, *Staphylococcus*, *Lactobacillus*, *Escherichia* or other member of the Enterobacteria, without being restricted to.

Typically, Firmicutes are gram-positive and have low GC-content. By "low GC-content" is meant that less than 52% of the base pairs in the bacterial genome are GC pairs. For example, gram-positive bacteria such as those of *Bacillus* and *Clostridium* contain 40% or less GC pairs in the genome.

Further suitable bacterial host cells are enteric bacteria such as those belonging to the order Enterobacteriales. Examples of such enteric bacteria are those being gram-negative such as of genus *Escherichia*. Specific examples are strains of *E. coli* such as TG1, W3110, DH1, XL1-Blue and Origami.

*E. coli* and enteric bacteria contain about 50% GC content in the genome and are therefore low GC content organisms.

Gram-positive and Gram-negative organisms are determined according to the well known gram-staining procedure. Gram-positive organisms are those that assume a violet color under standard gram-staining. Gram-negative organisms incorporate the counter stain rather than the primary gram-stain.

There are different mechanisms of CCR in Firmicutes and enteric bacteria which have been intensively studied in *Bacillus subtilis* and *E. coli* as model organisms (reference is made for example to J. Stulke et al., "Regulation of carbon catabolism in *Bacillus* species", Annu. Rev. Microbiol. (2000) 54: 849-880; Görke B. et Stülke J., "Carbon catabolite repression in bacteria: many ways to make the most out of nutrients", Nat. Rev. Microbiol. (2008) δ: 613-624; Gosset G. et al., Transcriptome analysis of Crp-dependent catabolite control of gene expression in *Escherichia coli*", J. Bacteriol., (2004) 186: 3516-3524, Martinez-Antonio A. et al., Identifying global regulators in transcriptional regulatory networks in bacteria" Curr. Opin. Microbiol. (2003) 6: 482-489). Though the overall mechanism of CCR is different the result is the same, namely that in the presence of a primary carbon source the various catabolic operons involved in uptake and phosphorylation of secondary carbon sources are repressed.

The recombinant bacterial host cell of the present invention is genetically altered to prevent repression of a carbon source inducible promoter controlling the expression of a heterologous nucleic acid sequence by inhibiting deactivation of the promoter specific transcriptional regulator protein in absence of said inducing carbon source.

Thus, in the recombinant bacterial host cell of the present invention the carbon source inducible promoter controlling the expression of the heterologous nucleic acid sequence is subject to carbon catabolite repression only. In the presence of a primary carbon source expression of the heterologous polypeptide is repressed by CCR. According to the present invention the carbon source inducible promoter is in its active state irrespective of the presence of the inducing carbon source unless carbon catabolite repression is stimulated by a more preferred primary carbon source.

The present invention, thus, provides for the production of heterologous polypeptide without the need of an inducer for inducing the promoter controlling the gene(s) encoding the polypeptide.

Generally, promoters suitable for the present invention are those which are subject to PTS and CCR in bacterial cells. In particular, the respective transcriptional regulator proteins are activators or antiterminators for the catabolic operon under control of said promoters. Such promoters are known in the art. Examples of promoters suitable for the present invention are given in the table below by reference to the respective operon:

| Operon | Regulator a) | Type b) | Inducer | Organism |
|---|---|---|---|---|
| sacPA | SacT | AT | sucrose | B. subtilis |
| sacB | SacY | AT | sucrose | B. subtilis |
| bgl PH | LicT | AT | β-glucosides | B. subtilis |
| licBCAH | LicR | A | oligo-β-glucosides | B. subtilis |
| levDEFG sacL | LevR | A | fructose | B. subtilis |
| mtlAD | MtlR | A | mannitol | B. subtilis |
| manPA-yjdF | ManR | A | mannose | B. subtilis |
| manR | ManR | A | mannose | B. subtilis |
| bglFB bglG | BglG | AT | β-glucosides | E. coli |
| lacTEGF | LacT | AT | lactose | L. casei | a): transcriptional regulator protein
b): A: activator AT: antiterminator

In the following the present invention is explained in more detail by reference to the mannose operon of *B. subtilis*.

*B. subtilis* can use a plurality of different mono- or di-saccharides as carbon source such as glucose, maltose, sucrose, mannose, mannitol, and fructose. These saccharides are taken up by the PTS system. Transport into the cell and phosphorylation are mediated by the enzyme EII specific for the respective saccharide.

As in many bacteria the preferred carbon source of *B. subtilis* is glucose. In presence of glucose uptake of any of the other saccharide subject to PTS is repressed by CCR.

Figure 2:
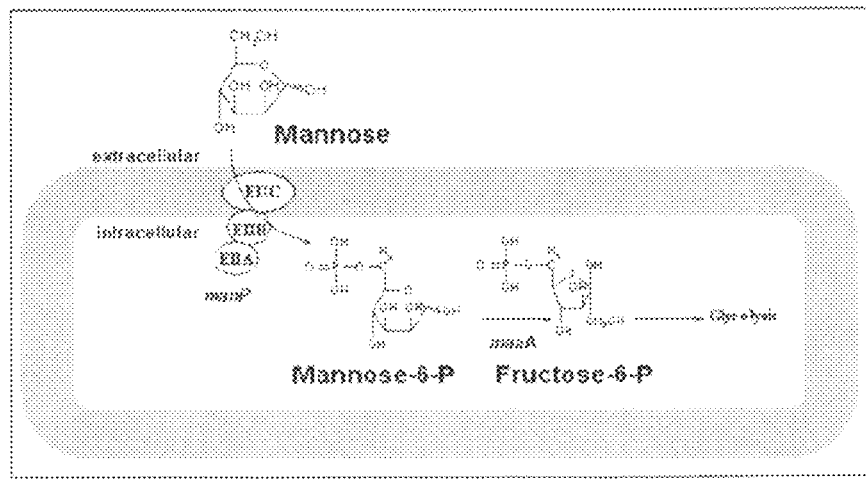
FIG. 2 a flow chart of the mannose catabolism with the transport into the cell, phosphorylation of mannose to mannose-6-phosphate during transport and conversion to fructose-6-phosphate.

The operon structure of mannose is shown in FIG. 1 and the transport of mannose into the cell and catabolism thereof in FIG. 2. The mannose operon of *B. subtilis* comprises three catabolic genes (Kunst F. N. et al., "The complete genome sequence of gram-positive bacterium *B. subtilis*", Nature (1997) 390: 249-256).

The first gene, manP, encodes the mannose specific EII enzyme referred to ManP. ManP effects the transport of mannose through the membrane and, simultaneously, phosphorylation of mannose to mannose-6-phosphate. The second gene, manA, encodes a mannose-6-phosphate isomerase which converts the mannose-6-phosphate to the corresponding fructose-6-phosphate. The function of the third gene, yjdF, is as yet unknown. Upstream and in the same orientation of these three genes, a regulatory gene, manR, is located which encodes for the transcriptional regulator protein referred to ManR.

The mannose-operon is a positively regulated catabolic operon and is controlled by two different promoters. One promoter, manR promoter (PmanR), is responsible for the transcriptional regulator protein ManR. The second promoter, manP promoter (PmanP), is responsible for the transcription of the genes manP-manA-yjdF (jointly referred to "manPA-yjdF"). In the presence of mannose and in the absence of glucose ManR binds to PmanP and activates the expression of manPA-yjdF. Surprisingly it has been found, that ManR is not only the transcriptional regulator protein for the manPA-yjdF-promoter but is an auto-regulator for manR itself.

FIG. 3 shows schematically the structure of the transcriptional regulator protein ManR and potential phosphorylation sites. As shown, ManR comprises two PRD (PTS regulatory domain) domains, one EIIA and EIIB domain as well as a HTH (Helix-turn-Helix) domain. PRDs are conserved regulatory domains present in transcriptional regulator proteins which can be phosphorylated in the course of carbon catabolism.

The EIIA and EIIB domains are binding sites of the phosphoryl group transferred by ManP, the EII transporter of the mannose operon. HTH is a structural motive in a protein capable of binding DNA.

In the absence of the inducer mannose the EIIA and EIIB and eventually PRDI domain of ManR is phosphorylated by ManP, the mannose specific EII of mannose operon, and thereby rendered inactive.

Consequently, according to the first approach of the present invention deactivation of ManR in the absence of the inducer, mannose, is prevented, if the phosphorylation sites in EIIA and/or EIIB of ManR are manipulated or the domains deleted, so that it cannot accept a phosphoryl group.

To this, gene manR, in the genome of the bacterial host cell, is genetically altered by deleting or manipulating the corresponding nucleic acid sequence encoding the respective phosphorylation site(s) in ManR.

Further, according to the second approach of the present invention deactivation of the promoters of the mannose operon is prevented by interruption of the mannose transport, which can be effected by deletion or inactivation of the gene encoding ManP, in the genome of the bacterial host cell.

These alterations can be done by altering or deleting in the bacterial host cell the coding sequence of the genes encoding the proteins involved in the phosphorylation of the transcriptional regulator protein, here, in the mannose operon, manR and/or manP.

Such genetically altered knock-out host cells can be prepared according to any of the various method known in the art for such purpose. For example, homologous recombination vectors containing homologous targeted gene sequences 5' and 3' of the targeted nucleic acid deletion sequence can be transformed into the host cell. Upon homologous recombination the desired knock-out cell can be produced.

Gene knock-out methods are well known in the art. For example, gene inactivation by insertion of a polynucleotide has been described in, for example, Röder D. L. et al., "Marker-exchange mutagenesis of a pektate lyase isozyme gene in *Erwinia* chrys anthemy" J. Bacteriol. (1985) 164 (1: 51-56). Specific mutations or deletions in a gene can be constructed using cassette mutagenesis, for example, as described in Wells J. A. et al., "Cassette mutagenesis: an efficient method for generation of multiple mutations at defined sites", Gene (1985) 34 (2-3): 315-323; whereby direct or random mutations are made in a selected portion of a gene, and then incorporated into the chromosomal copy of the gene by homologous recombination.

It has been found by the present inventors that the promoters regulating the mannose operon, namely PmanR and PmanPA-yjdF are strong promoters which are, therefore, promising candidates for the production of heterologous polypeptides. However, mannose, the carbon source inducing these promoters, is a high price sugar which, as yet, restrict the use of mannose inducible promoters.

Since according to the present invention for expression of a heterologous polypeptide in a bacterial host cell no inducing carbon source is necessary for initiating expression also the use of promoters such as the mannose promoters are competitive not only in view of strongness but also in costs.

Consequently the present invention relates also to the use of the promoters of the mannose operon, PmanR and PmanPA-yjdF, as a promoter for controlling a heterologous nucleic acid sequence encoding for a target polypeptide in the recombinant bacterial host cell of the present invention.

The nucleic acid sequence from *B. subtilis* comprising the promoter region of the manP promoter as used in various expression vectors like pSUN284.1 is shown in FIG. 5 with the transcription start site at an adenine nucleotide being highlighted, the −35 and −10 boxes in italics and bold, and the end of manR marked by an arrow and the restriction sites BglII, XbaI, NdeI and NruI underlined. The start codon of the reporter gene lacZ is indicated.

The nucleic acid sequence obtained from *B. subtilis* comprising the promoter region of manR promoter is shown in FIG. 4 with the transcription start site being highlighted, the −10 and −35 boxes being italics and bold, the start of manR gene being indicated by an arrow and the HindIII restriction sites being in bold and underlined and the putative cre sequence being underlined.

With "promoter regions of the mannose operon" are meant the promoter regions which regulate expression of manPA-yjdF as well as of manR with or without the cre sequence.

The "manPA-yjdF promoter" as referred to herein consists essentially of the −35 region, the −10 region (Pribnow box), the transcription start site, and the ManR binding site.

The "manR promoter" as referred to herein consists essentially of the −35 regions, the −10 region, the transcription start site and the ManR binding site and, optionally, a cre sequence.

Figure 6:
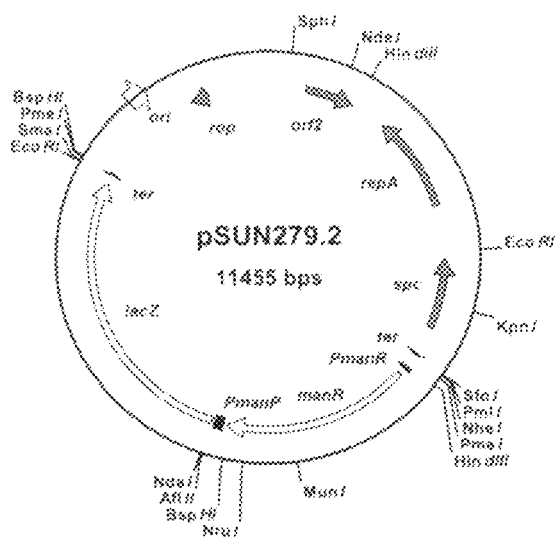
FIG. 6 shows the plasmid map of the expression vector pSUN279.2.

The cre sequence (catabolite repressive element) is a conserved 14 nucleotides long DNA sequence to which binds CcpA (catabolite control protein A), the global regulator protein of CCR in Firmicutes. The mechanism of catabolite repression and activation in *B. subtilis* is shown in FIG. 6. By the binding of CcpA, complexed by Serin-46 phosphorylated HPr (histidine protein) to the cre sequence the promoter is repressed. This represents a second mechanism of catabolite repression of the mannose operon. By this way, the expression of the regulator gene manR is repressed in the presence of glucose. In consequence, this inhibits an activation of the manP promoter. In the presence of glucose cells take up glucose via PtsG, a PTS-dependent transport system similar to the EII mannose transporter. In the cell the intermediates fructose-6-phosphate (Fru-6-P) and fructose-1,6-biphosphate (Fru-1,6-DP) accumulate and stimulate the HPr-kinase. HPr-Kinase (HPrk) phosphorylates HPr at Serin-46. Ser-46-HPr forms a complex with the DNA binding protein CcpA which binds to the so-called cre-sites present in many catabolite repressed and catabolite activated promoters of *B. subtilis*. Is the cre site downstream of the −10 promoter sequence or overlapping the −10 sequence the binding of the Ser-46-HPr/CcpA complex inhibits expression from this promoter. This situation is found at the manR promoter (FIG. 4).

The nucleic acid sequence comprising the promoter region of manPA-yjdF preferably comprises the nucleic acid sequence of FIG. 5 from bp−80 to the start codon of lacZ (SEQ ID NO. 1) and more preferably the nucleic acid sequence of FIG. 5 from bp−80 and inclusive bp−1, i.e. upstream of the transcription initiation site A at bp+1 (SEQ ID NO. 2).

The nucleic acid sequence comprising the promoter region of manR preferably comprises the nucleic acid sequence of FIG. 4 from bp−122 to the start codon of manR (SEQ ID NO.3), more preferably, the nucleic acid sequence of FIG. 4 from bp−122 and bp+7, i.e. inclusive the putative cre-sequence, (SEQ ID NO. 4), and, in particular, the nucleic acid sequence of FIG. 4 from bp−122 and bp−1, i.e. upstream of the transcription initiation site G at bp+1 (SEQ ID NO. 5). Both, the promoter regions of manP and manR, comprise a binding site for the transcriptional regulator protein ManR (marked in FIG. 4 as IRI-R and in FIG. 5 as IRI-P), which is the transcriptional activator for the promoters of the mannose operon.

According to a further aspect, the present invention relates to such a genetically altered bacterial host cell comprising a vector with a nucleic acid sequence encoding for a polypeptide of interest operably linked to a carbon source inducible promoter, wherein the promoter of the vector is regulated by the transcriptional regulator protein for which the bacterial host cell has been genetically altered to be unable to deactivate in the absence of the carbon source specific for said transcriptional regulator protein.

Referring to the mannose operon above, the promoter of the vector can be the PmanR or PmanPA-yjdF, for example, any of the sequences SEQ ID NOs. 1 to 5 as well as any of the table above.

According to an embodiment of the present invention in the vector used in the present invention the genetically altered gene encoding for the respective transcriptional regulator protein incapable to bind a phosphoryl group transferred by the respective EII, can be incorporated. Consequently, in the recombinant bacterial host cell the transcriptional regulator protein is not only expressed by the chromosomal gene but also by the corresponding gene integrated into the vector which results in a higher concentration of transcriptional regulator protein and improved induction. For example, when the promoter of the vector is a promoter of the mannose operon, the gene manR can be integrated into the vector, wherein the nucleotide sequence coding EIIA domain has been deleted (manRΔEIIA).

A vector suitable for the present invention is preferably an autonomously or self-replicating plasmid, a cosmid, a phage, a virus or a retrovirus. A wide variety of host/vector-combinations may be employed for the present invention. Useful expression vectors, for example, may consist of segments of chromosomal, non-chromosomal and/or synthetic nucleic acid sequences.

Suitable vectors include vectors with specific host range such as vectors specific for e.g. *B. subtilis* and *E. coli*, respectively, as well as vectors with broad-host-range such as vectors useful for gram-positive bacteria and gram-negative bacteria. "Low-copy", "medium-copy" as well as "high-copy" plasmids can be used.

For example, in *B. subtilis* a low-copy plasmid is pAMbeta1, medium copy plasmids are pBS72 derivatives and a high copy plasmid is pUB110. Useful vectors for, e.g. expression in *E. coli* are pBR322, pUC18, pACYC177, pACYC184, pRSF1010 and pBW22 or derivatives thereof such as plasmid pBLL 15 or plasmid pAKL15E.

The genetically altered bacterial host cell of the present invention is incapable of deactivating the transcriptional regulator protein controlling the promoter in the absence of the inducing carbon source of said promoter. Since the promoter of the vector is controlled by the same transcriptional regulator protein as the respective chromosomal promoter expression of the heterologous nucleic acid sequence encoding for the target polypeptide continues, even in absence of inducing carbon source.

Further, provided with the present invention is a method for producing a heterologous polypeptide in the genetically altered bacterial host cell of the present invention comprising the steps of
a) culturing under conditions allowing expression of the polypeptide, the genetically altered bacterial host cell of the present invention transformed with a vector comprising the nucleic acid sequence encoding the polypeptide operably linked to a promoter, wherein the promoter of the vector is regulated by the transcriptional regulator protein which can not be deactivated in the absence of the carbon source specific for the transcriptional regulator protein, and
b) recovering the polypeptide from the cells or from the cell culture.

According to the present invention expression of the target polypeptide starts automatically at the point of time when the medium runs out of the primary carbon source, or the concentration of primary carbon source decreases below a level required for CCR.

For allowing the cells to grow after induction, the primary carbon source can be fed to the medium further on at a level which does not allow carbon catabolite repression. For example, primary carbon source is fed in an amount which is immediately consumed by the cells so that in the fermentation broth essentially no primary carbon source is present which could stimulate CCR.

Generally it can be said that if the amount of primary carbon source present in the medium exceeds 1.0 g/l carbon catabolite repression is observed, whereas, if the amount is 0.01 g/l or less there is no carbon catabolite repression.

Since the borderline of carbon catabolite repression and induction of the promoter correlates with the growth rate of the cells, which in turn, correlates to the amount of primary carbon source fed to the medium, or present in the medium, the amount of primary carbon source, which does not cause carbon catabolite repression, can be adjusted by monitoring the growth rate. If at a given growth rate carbon catabolite repression occurs the amount of primary carbon source added to the medium must be reduced, thereby reducing the growth rate until a value at which no carbon catabolite repression is observed.

For most fermentation processes in the induction phase adjustment of the primary carbon source addition to an amount is suitable which results in a specific growth rate of $\mu \leq 0.2$ h$^{-1}$.

In any case, for a specific fermentation process a suitable value for the specific growth rate $\mu$ can be readily determined by routine work.

The vectors used, as well as construction and transformation of the host are as defined above.

As cell culture system continuous or discontinuous culture such as batch culture or fed-batch culture can be applied in culture tubes, shake flasks or bacterial fermentors etc. Preferably, in the induction phase when the target polypeptide is expressed, the primary carbon source is exponentially fed to the cultivation medium.

For culturing the genetically altered bacterial host cells conventional media as known in the art can be used such as complex media like "nutrient yeast broth medium", a glycerol containing medium as described by Kortz et al., J. Biotechnol. (1995) 39: 59-65, a mineral salt media is descripted by Kulla et. al. Arch. Microbiol. (1983) 135: 1, a LB-medium as described by Bertani et al., J. Bacteriol. 1951) 62: 293-300, or a batch medium for *E. coli* fermentation as described by Wilms et al., Biotechnol. Biong. (2001) 73: 95-103.

The medium comprises a suitable carbon source, for example a sugar such as glucose for growing the host cell to a desired cell density. As carbon source a primary carbon source for the respective host cell is used which is different from the inducer, which is a secondary carbon source for said host cell.

The medium might be modified as appropriate, for example, by adding further ingredients such as buffers, salts, vitamins, amino acids, antibiotics or other micronutrients as are generally known to those of skill in the art. As well different media or combinations of media can be used during the culturing of the cells.

In one embodiment of the invention casamino acids are added to the culture medium. It has been found, that the presence of casamino acids in the medium can help to suppress basal level expression.

Typically, the casamino acids can be added in an amount of 0.05% to 0.1% (w/v).

According to an embodiment of the present method for producing a heterologous polypeptide a bacterial host cell can be used comprising the genes encoding for the mannose operon in its genome, that is for which mannose is a secondary carbon source, and for which, for example, glucose is a primary carbon source. To be suitable as a host for the present method the bacterial cell is rendered incapable to deactivate ManR, the transcriptional regulator protein controlling the promoters of the mannose operon.

For example, the nucleotide sequence manP coding for ManP can be deleted, thereby inhibiting deactivation of ManR by phosphorylation via ManP.

Into the manP deleted bacterial host cell a vector is introduced comprising promoter PmanR or promoter PmanP operably linked to the nucleic acid sequence encoding the target polypeptide.

The recombinant bacterial host cell is grown in a culture medium suitable for said bacterial host cell, wherein the culture medium can contain glucose and/or glucose can be fed to the culture medium in an amount sufficient to allow the bacterial host cell to multiplicate and to repress expression of the target polypeptide by glucose mediated carbon catabolite repression of the mannose promoter contained in the vector.

As soon as the glucose level of the medium drops below a value required for carbon catabolite repression, carbon catabolite repression of the mannose promoter of the vector is released and the mannose promoter starts expression of the polypeptide without the need of induction by mannose. Further, since in the bacterial genome the nucleic acid sequence encoding for ManP is deleted the mannose promoter cannot be deactivated by phosphorylation via ManP. Thus, the present method allows expression of a target polypeptide under control of a specific carbon source inducible promoter without the presence of the inducing carbon source.

Typically, during the induction phase in the fermentation process using a bacterial host cell transformed with a vector comprising a promoter of the mannose operon glucose, being the primary carbon source of the promoters of the mannose operon, can be fed to the fermentation medium in an amount resulting in a specific growth rate $\mu 0.2 \ h^{-1}$. Further, exponential feed is preferred.

In principle, the explanations set out above with respect to the first alternative of the present invention requiring no inducing carbon source for inducing the promoter at all, are also applicable on the second alternative of the present invention according to which the amount of carbon source necessary for induction is reduced.

The present invention is advantageous in that the promoters controlling the expression of the heterologous nucleic acid sequence encoding for the target polypeptide allow a tight regulation.

Addition or presence of the inducing carbon source is not necessary.

According to the first alternative of the present invention the promoter is in the active state even without inducing carbon source, that is in the absence of inducer.

The mannose promoter PmanP of the mannose operon of *B. subtilis* has been proven to be a strong promoter. A detailed discussion of the mannose operon is given in Sun T. et al. "Characterization of a mannose utilization system in *Bacillus subtilis*" J. Bacteriol 192, 2010, 2128-2139 which is herein incorporated by reference.

The strong control properties of gene expression by PmanP qualifies this promoter for the heterologous production of valuable polypeptides. However, it has been found by the present invention that a *B. subtilis* expression system involving the mannose operon requires a high amount of mannose in order to obtain permanent high expression rates. It is assumed that the reason of the rapid consumption of the inducer mannose is that mannose is one of the favourite carbon sources of *B. subtilis*. However, mannose is a rather expensive sugar, making such an expression system economically unfeasible for large scale industrial applications.

In order to optimize such an expression system for industrial application the inducer must not be metabolized.

According to the present invention this is achieved by manipulation or preferably disrupting the mannose-6-phosphate isomerase gene manA in the chromosomal genome of a host cell for rendering the host cell incapable to convert the incoming mannose-6-phosephate to fructose-6-phosphate that subsequently enters glycolysis.

Such an expression system requires by far less inducer and, nevertheless, high expression rates can be achieved.

As set out above a particular advantageous expression system is one which is auto-inducible, that is one which does no longer need any inducer. According to a preferred embodiment of the present invention such an auto-inducible expression system is obtained by rendering in the mannose operon of the genome of the bacterial host cell the gene manP incapable of deactivation of the regulator protein ManR by preventing phosphorylation of the EIIB and EIIA-like domains of ManR by ManP.

Preferably, the chromosomal gene manP is deleted (knockout mutant).

In such an expression system the PmanP promoter is only under regulatory control by CCR committed by glucose. Not until glucose becomes limiting the regulator ManR can bind to its operator system and start the expression. Such an auto inducible expression system is very valuable for industrial applications, since virtually no premature gene expression takes place.

For example, in fed batch fermentation virtually no unwanted expression is observed in the batch phase and no addition of any inducer is necessary to get high expression levels throughout the fed batch phase. Such an expression system is particularly suitable for high cell fermentations and alloys high expression rates to be obtained.

The novel expression system provided by the present invention, in particular the novel auto-induction system, does make a considerable contribution to improve product yield and to reduce the costs associates with its technical application.

As shown in the following examples the present invention provides for a production of heterologous polypeptides by culturing the genetically altered bacterial host cell of the present invention wherein during the growth of the genetically altered bacterial host cells and prior to induction only very low or no premature expression of the polypeptide occurs, that is, there is essentially no leakiness of the promoter controlling the expression of the genes encoding for the polypeptide. Further, production of the polypeptide starts immediately upon auto-induction in high rates of productivity with a high end productivity.

Also shown is an example for the further alternative of the present invention wherein in the genome of the bacterial host cell harboring a vector with a mannose inducible promoter and a heterologous nucleic acid sequence, the gene is deleted, encoding for the mannose-6-phosphate isomerase.

The foregoing description will be more fully understood with reference to the following examples. Such examples are however exemplary of methods of practicising the present invention and are not intended to limit the scope of the invention.

I) Isolation and Identification of Promoter Regions of manR Promoter and manP Promoter of Mannose Operon If not stated otherwise the following materials and methods has been used:

Bacterial Strains and Growth Conditions

*E. coli* JM109 (Yanisch-Perron C. et al., Gene 33, 1985, 103-119) and *Bacillus subtilis* 3NA, a non-sporulating *B. subtilis* strain with a mutation in the spo0A gene, (Michel J. F. et al., J. Appl. Bacteriol. 33, 1970, 220-227) were used as main hosts for cloning and expression. Further strains used for fermentation experiments were *B. subtilis* 3NA mutant strains TQ281 (spo0A Δ manA:: ermc) (Sun T. et. al., J. Bacteriol. 192, 2010, 2128-2139) and TQ356 (spo0A Δ manP:: ermc) (see below II, Experiment 4, b). Strains were grown at 37° C. in LB medium (Bertoni G., J. Bacteriol. 62, 1951, 293-300).

Selection conditions were as follows: 100 µg ml$^{-1}$ ampicillin, 100 µg ml$^{-1}$ spectinomycin, 5 µg ml$^{-1}$ erythromycin.

For induction of the mannose promoter, sterile filtered or autoklaved D-mannose was added to a final concentration of 0.2% w/v.

Materials

All chemicals were obtained from Sigma-Aldrich (Taufkichen, Germany), Fluka (Buchs, Germany) or Merck (Darmstadt, Germany). Synthetic DNA oligonucleotides were purchased from Eurofins MWG Operon (Ebersberg, Germany). Restriction enzymes and DNA modifying enzymes were purchased from Roche Applied Science (Mannheim, Germany) or New England Biolabs. (Frankfurt am Main, Germany). PCRs were run with High Fidelity-DNA polymerase from Fermentas (ST. Leon-Rot, Germany) on a MiniCycler TM from MJ Research Inc. (Walthan, Mass., USA).

Preparation of DNA and Transformation

DNA-isolation from *E. coli* and *B. subtilis* or from agarose gel were carried out with DNA preparation kits of Qiagen (Hilden, Germany) or Roche (Mannheim, Germany) as described by the manufacturer. Standard molecular techniques were used throughout the examples.

*E. coli* was transformed with plasmid DNA as described by Chung C. T. et al., Proc. Natl. Acad. Sci. USA 86, 1989, 2172-2175. *B. subtilis* was transformed with plasmid DNA according to the modified "Paris method" (Harwood C. R. Molecular Biological Methods for *Bacillus*, 1990, John Wiley & Sons Ltd., England).

β-Galactosidase Activity Measurement 0.1 ml of the cells to be examined were treated with 900 μl Z-buffer and 10 μl toluene for 30 min at 37° C. The β-galactosidase activity was determined with o-nitrophenyl-β-galactopyranoside at 22° C. according to Miller's method (Miller J. H., 1972, experiments in molecular genetics, Cold Spring Harbor, N.Y.).

Oligonucleotides (Primers) Used

TABLE 1

| Oligo-nucleotide | Sequence | Purpose |
|---|---|---|
| SEQ ID NO 6 s4693 | 5'-AAA AAA ACG CGT GTT TAA ACT GAA TTT CTG CTG AAT ATA CA-3' | PCR amplification of manR from *B. subtilis* |
| SEQ ID NO 7 s4694 | 5'-AAA AAA TCT AGA AAG TGT GAA TAA TAA GAT CTT G-3' | PCR amplification of manR from *B. subtilis* |
| SEQ ID NO 8 s4802 | 5'-AAA AAA ACT AGT GTT TAA ACA GGG AAA AAT GCC TTT ATT AC-3' | Forward primer for amplification of $P_{manP}$ |
| SEQ ID NO 9 s4833 | 5'-AAA AAA GTT TAA ACC CCT GGC GAA TGG CGA T-3' | Amplification of spc from plasmid pDG1730 |
| SEQ ID NO 10 s4835 | 5'-AAA AAA GAA TTC ATT AGA ATG AAT ATT TCC CAA AT-3' | Amplification of spc from plasmid pDG1730 |
| SEQ ID NO 11 s4956 | 5'-AAT GCG TCG AGA CCC CTG TGG GTC TCG TTT TGG ATC CGG CGC CCA CGT GGC TAG CC-3' | Insertion of tufA terminator |
| SEQ ID NO 12 s4957 | 5'-TTA GGC TAG CCA CGT GGG CGC CGG ATC CAA AAA CGA GAC CCA CAG GGT CTC GAC GC-3' | Insertion of tufA terminator |
| SEQ ID NO 13 s5006 | 5'-Cy5-TAG CCT TTT TTA TAG TTG TTC AGC CAC TGT-3' | Labeled primer for primer extension |
| SEQ ID NO 14 s5007 | 5'-Cy5-ATC CAC GCC ATA ATG CAT GCC GCC ATT AAT-3' | Labeled primer for primer extension |
| SEQ ID NO 15 s5019 | 5'-tta agC TCT AAG GAG GAT TTT AGA ATG GCT AAA GAA AAA TTCg-3' | tufA TI-Region |
| SEQ ID NO 16 s5020 | 5'-tta agG AAT TTT TCT TTA GCC ATT CTA AAA TCC TCC TTA AGA Gg-3' | tufA TI-Region (compl.) |
| SEQ ID NO 17 s5069 | 5'-AAA AAA GAA TTC GAT ATC AGA TCT ACG CGT TAA CCC GGG C-3' | PCR erythromycin resistance gene |
| SEQ ID NO 18 s5070 | 5'-AAA AAA CAA TTG AAT CGA TTC ACA AAA AAT AGG-3' | PCR erythromycin resistance gene |
| SEQ ID NO 19 s5071 | 5'-AAA AAA AGA TCT CAT GGC AGG GCT TGA GAA-3' | manA deletion |
| SEQ ID NO 20 s5072 | 5'-AAA AAA GAA TTC TTA TTT ACC TCT GTG CTT CTT-3' | manA deletion |
| SEQ ID NO 21 s5097 | 5'-Cy5-CACTGTACCCTATCTGCGAAA-3' | Labeled primer for primer extension |
| SEQ ID NO 22 s5098 | 5'-Cy5-ATTGAGATAATCCTCGATCACTT-3' | Labeled primer for primer extension |
| SEQ ID NO 23 s5139 | 5'-aaa aaa tga tca TTA CTT GTA CAG CTC GTC-3' | f-Primer PmanP-eGFP |
| SEQ ID NO 24 s5156 | 5'-aaa aaa tga tca ccg gtC GAT TGC ACA ATT AAA GG-3' | r-Primer PmanP-eGFP |

TABLE 1-continued

| Oligo-nucleotide | Sequence | Purpose |
|---|---|---|
| SEQ ID NO 25 s5203 | 5'-GATATCCTGCACCATCGTC-3' | Backward primer for amplification of P$_{manP}$ for promoter study |
| SEQ ID NO 26 s5208 | 5'-GGTACCATTTCTTGCTGAATA-3' | Amplification of P$_{manR}$-region from pSUN279.2 |
| SEQ ID NO 27 s5209 | 5'-CTTAAGCCTGTCAGTATCTACTTGAG-3' | Amplification of P$_{manR}$-region from pSUN279.2 |
| SEQ ID NO 28 s5234 | 5'-aaa aaa ccg CTC GTC TTC CTA AGC ATC CT-3' | f-Primer rep (pUB110) |
| SEQ ID NO 29 s5235 | 5'-aaa aaa gaa tTC GAG ATC AGG GAA TGA GTT T-3' | r-Primer rep (pUB110) |
| SEQ ID NO 30 s5236 | 5'-tta agA ATT AAA GGA GGA ATT CAA AAT GGC AGA CAA TAA CAA Ag-3' | gsiB TI-Region |
| SEQ ID NO 31 s5237 | 5'-gat ccT TTG TTA TTG TCT GCC ATT TTG AAT TCC TCC TTT AAT Tc-3' | gsiB TI-Region (compl.) |
| SEQ ID NO 32 s5262 | 5'-AAA'AAA GCT AGC GTT AAA ACA AAA AGC GATT TTA ATG AGC TG-3' | Forward primer for amplification of P$_{manP}$ |
| SEQ ID NO 33 s5362 | 5'-GGT ACC CCC GGG TAG CCT GGA TGG ATC AGA A-3' | manP deletion |
| SEQ ID NO 34 s5363 | 5'-ACT AGT GAA TTC CTT TTC CAA TCG CA-3' | manP deletion |
| SEQ ID NO 35 s5407 | 5'-AAA AAA GGC GCC GCT AGC TGG AGA ATA TAA CGG TT-3' | manP deletion |
| SEQ ID NO 36 s5408 | 5'-ACA CTC CTT AAG TCT AGA AA-3' | manP deletion |
| SEQ ID NO 37 s5617 | 5'-GGA GGG GAG AAA ACA CCT A-3' | manA deletion |
| SEQ ID NO 38 s5618 | 5'-AAA AAA GAT ATC TCA AGA AAA TCC CCC GCT TT-3' | manA deletion |
| SEQ ID NO 39 s5932 | 5'-AAA AAA GCT AGC GTT AAA ACA GTA TAA AAA TCG CTT TTT TCC-3' | Forward primer for amplification of P$_{manR}$ |
| SEQ ID NO 40 s5933 | 5'-AAA AAA GCT AGC GTT AAA ACC GGA AGC TTC GGT AAA AA-3' | Forward primer for amplification of P$_{manR}$ |
| SEQ ID NO 41 s5934 | 5'-GTG CAG GAG CTC GTT ATC-3' | Reverse primer for amplification of P$_{manR}$ |

Experiment 1:

Isolation of DNA fragment carrying the promoter regions of the mannose operon and determination of transcription initiation sites of manR promoter and manP promoter.

Chromosomal DNA of *Bacillus subtilis* 168 was isolated by using DNEASY® Blood & Tissue Kit of Qiagen (Hilden, Germany).

A DNA fragment of about 2.3 kb with the complete manR gene and the manR promoter and the intergenic region between manR and manP with the manP promoter was amplified from the obtained DNA by PCR using primer s4693/s4694.

The obtained DNA fragment of about 2.3 kb was used for a primer extension experiment for determining the transcription initiation sites of manR promoter and manP promoter.

For isolation of mRNA for primer extension a shuttle factor was constructed from the *E. coli* vector pIC20HE (Altenbuchner et al., 1992, Methods Enzymol. 216, 457-466) and the *B. subtilis* vector pUB110 (MacKenzie et al., 1986, Plasmid 15, 93-103). The vector contained the lys gene as reporter gene, which codes for the mature form of lysostaphin from *Staphylococcus simulans* (Recsai et al., 1987, Proc. Natl. Acad. Sci. USA 84, 1127-1131).

Into this high copy pUB110 derivative the 2.3 kb DNA fragment was cloned upstream to the lysostaphin gene. The resulting plasmid was named pSUN178.4 and introduced into *Bacillus subtilis* 3NA.

*Bacillus subtilis* 3NA with plasmid pSUN178.4 was grown in LB medium with kanamycin. In the exponential growth phase the culture was induced with 0.2% w/v mannose. After 1 hour growth at 37° C. the induced and non-induced cells were harvested. Total RNA was isolated with the Qiagen-RNeasy Mini Kit.

With Cy5 at the 5'-end labeled primers s5006, s5007, s5097 and s5098 were used. Primer s5006 and s5007 hybridized respectively from +21 to +50 and from +76 to +105 with respect to the start codon of lysostaphin gene. Primer s5097 and s5098 hybridized respectively from +81 to +101 and from +131 to +153 with respect to the start codon of manR.

The same primers were used for the sequencing reaction of plasmid DNA of pSUN178.4, which served as size standard. The AMV-Reverse Transcriptase and T7-DNA polymerase from Roche were used, respectively, for the reverse transcription and DNA sequencing. The products of reverse transcription and sequencing were analyzed on a denaturating polyacrylamide sequencing gel (GE healthcare). All other reagents used were provided by Amersham Pharmacia Biotech Auto Read Sequencing kit.

The transcription initiation site of manP-promotor was determined by using primer s5006. DNA sequence reactions of the plasmid pSUN 178.4 with the same primer were prepared and run on the same denaturing gel for comparison.

FIG. 5 shows the DNA sequence around the manP promoter with the transcription initiation site at A (adenine nucleotide) being highlighted. The deduced −10 and −35 boxes are in italics, the end of the manR gene is marked by arrows, restriction sites for BglII NruI, XbaI, NdeI AflIII are underlined. IRI-P indicates an imperfect inverted repeated sequence, the putative ManR binding site.

The transcription initiation site of manR promoter was determined with RNA isolation and DNA sequencing being carried out as described above with respect to manP promoter except that primer s5098 was used which binds in the manR gene.

In FIG. 4 the DNA sequence of the manR promoter region is shown with the transcription initiation site at G (guanine nucleotide) being highlighted, the deduced −10 and −35 boxes in italics, ribosomal binding site (RBS) underlined, and the start of the manR gene, respectively, being indicated by an arrow. The restriction sites and a putative cre sequence are underlined. IRI-R indicates an imperfect inverted repeated sequence, the putative ManR binding site.

The transcription from the manR promoter and in particular from the manP promoter was strongly increased when the cells were induced by mannose as was seen by the much stronger signals in the primer extension experiment.

The primers used are shown in table 1 above.
Experiment 2

The primer extension experiment according to Experiment 1 located the transcription initiation site of the manP promoter near the 3'-end of the intergenic region between manR and the beginning of manP. For determining the manP promoter region more precisely the 2.3 kb DNA fragment was shortened step-by-step by PCR-amplification, the obtained sequence fragments of different lengths cloned back to the same basic expression vector and expression was studied.

a) Construction of Basic Expression Vector

An expression vector with promoterless lacZ as reporter gene was constructed. The expression vector was designed as a shuttle vector capable of replicating both in *B. subtilis* and in *E. coli* and named pSUN272.1.

The reporter gene lacZ was cut with NdeI and XmaI from pLA2 (Haldimann A. et al, 2001, J. Bacteriol. 183, 6384-6393) and ligated into pJOE5531.1, a derivate of the rhamnose inducible expression vector pWA21 (Wegerer et al., 2008, BMC. Biotechnol. 8, 2) which contained the *B. subtilis* tufA transcription terminator at the XmaI site. Into this plasmid a pair of oligonucleotides s4956/4957 was inserted between the AflIII/MunI restriction sites in order to add the same tufA transcription terminator upstream of lacZ. So the "reading through" from plasmid promoters into lacZ as well as "reading through" out of lacZ into the flanking plasmid sequences was avoided by the terminators. A spectinomycin resistance gene spc for both *E. coli* and *B. subtilis* was amplified from plasmid pDG1730 (Geurout-Fleury et al., 1996, Gene 180, 57-61) with oligonucleotides s4833/4835 and inserted into the plasmid obtained above. In addition, the *E. coli* vector part was shortened by deleting a BspHI/HindIII fragment. Subsequently, an EcoRI/SphI fragment with the replication region of *B. subtilis* pMTLBS72 (Lagodich et al., 2005, Mol. Biol. (Mosk) 39, 345-348) was ligated into the plasmid.

Figure 7:
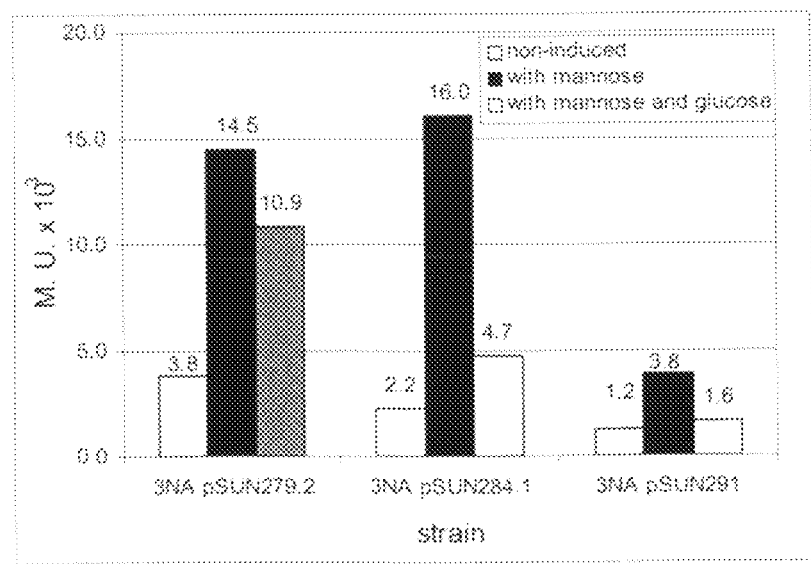
FIG. 7 shows β-galactosidase activities of *B. subtilis* 3NA containing the plasmids pSUN279.2, pSUN284.1 and pSUN291, respectively.

The 2.3 kb DNA fragment obtained in Experiment 1 was inserted into pSUN272.1 in front of lacZ by digesting with AR and NheI and ligation, thereby obtaining expression vector pSUN279.2 with the plasmid map as shown in FIG. 7. The primers used are shown in table 1 above.

b) Determination of Expression Efficiency of Vector pSUN279.2

The plasmids pSUN279.2 and pSUN272.1 obtained in a) above were brought into *B. subtilis* 3NA. The latter served as background control. The *B. subtilis* 3NA strains carrying one or the other plasmid were grown in LB medium with spectinomycin and in the exponential growth phase either 0.2% mannose, 0.2% mannose plus 0.2% glucose or no sugar (uninduced control) were added to the cultures for induction. After one hour induction the β-galactosidase activity of the cells was determined through Miller's assay. The results are shown in FIG. 8

The non-induced culture of *B. subtilis* containing pSUN279.2 showed already a quite high basal level of β-galactosidase activity. The presence of mannose resulted in a further 4-fold increase of β-galactosidase activity whereas the activity with mannose and glucose was reduced but was still quite above the basal level. The results clearly indicate that the promoter activity seen in pSUN279.2 could originate from the region between manR and manP, from the region upstream of manR or from both.

Therefore, the upstream region of manR as well as most part of manR were both deleted from pSUN279.2 by cutting the 2.3 kb DNA fragment of pSUN279.2 as shown in FIG. 7 between SfoI and NruI to give plasmid pSUN284.1.

*B. subtilis* 3NA was transformed with this plasmid pSUN284.1 and the expression efficiency determined as set out above. The result is shown in FIG. 8. As can be seen from FIG. 8 this manR deleted vector pSUN284.1 in *B. subtilis* 3NA showed only about half of the basal level of β-galactosidase activity compared to pSUN279.2 in *B. subtilis* 3NA, an even stronger increase by mannose induction and again a stronger reduction in the presence of glucose. These results prove that the manP promoter is located between manR and manP and show that the chromosomal copy of manR is sufficient for regulating all manP promoter copies on the low copy plasmids.

c) Localization of manP Promoter Region

For localizing the promoter region of manP in addition to the shortened DNA fragment of pSUN284.1 further shortened sequence fragments were prepared from the 2.3 kb DNA fragment by amplifying DNA fragments by PCR shortened at different positions upstream to the transcription initiation site of manP promoter and inserting the fragments in pSUN272.1 as shown in FIG. 5.

Deletion down to by −81 and by −80 upstream to the transcription initiation site of manP resulted in a second deletion sequence comprising SEQ ID NO. 1.

A further deletion was carried out down to by −41 and by −40 upstream to the transcription initiation site of manP (third deletion sequence).

Plasmids comprising the second deletion sequence, pSUN290, and the third deletion sequence, pSUN297.5 were constructed in a similar way as plasmid pSUN284.1 in 2b) above, by inserting the PCR products amplified with primers s4802/s5203 and s5262/s5203, respectively, into pSUN272.1 via restriction enzymes EcoRV and NheI.

The plasmids were inserted into *B. subtilis* 3NA and cultured as set out above in b) After 1 hour induction the β-galactosidase activity of the cells was determined as set out in b) above. The results are shown in FIG. 9.

As shown in FIG. 9 none of the strains with pSUN290 and pSUN284.1 showed a significant difference concerning induction of lacZ by mannose. However, in *B. subtilis* 3NA comprising pSUN297.5, induction by mannose was completely abolished and the basal expression level was nearly 0. From these results follows that the ManR binding site of the manP mannose promoter region is located between by −80 and −35 with respect to the transcription initiation site of manP.

Experiment 3: Determination of manR Promoter a) Identification of Cre Sequence

Since most CCR in Firmicutes is mediated through catabolite control protein A (CcpA) a search for the respective binding sites (cre sequence) was carried out in the whole mannose operon using the DNA alignment function in the Clone Manager program. For the alignment the cre consensus sequence SEQ ID NO 42 5'-VWVTGNAARCGNWW-WCAWW-3' was used.

Only in the promoter region of manR one putative cre sequence was found as shown in FIG. 4 which is located downstream to the −10 box.

b) Evaluation of Expression Efficiency of manR Promoter

For evaluating the expression efficiency of the manR promoter an expression vector like pSUN284.1 was constructed as set out above and named pSUN291. To this, a DNA fragment including the putative manR-promoter and about 600 bp upstream of manR was amplified with primer s5208/s5209 and linearized plasmid DNA pSUN279.2 as template and inserted in front of lacZ in plasmid pSUN272.1, by digesting with KpnI and AflIII and ligation.

The DNA-sequence is shown in FIG. 4.

Plasmid pSUN291 was introduced into *B. subtilis* 3NA and the β-galactosidase activity was measured as set out above in experiments 2 b).

Figure 10:
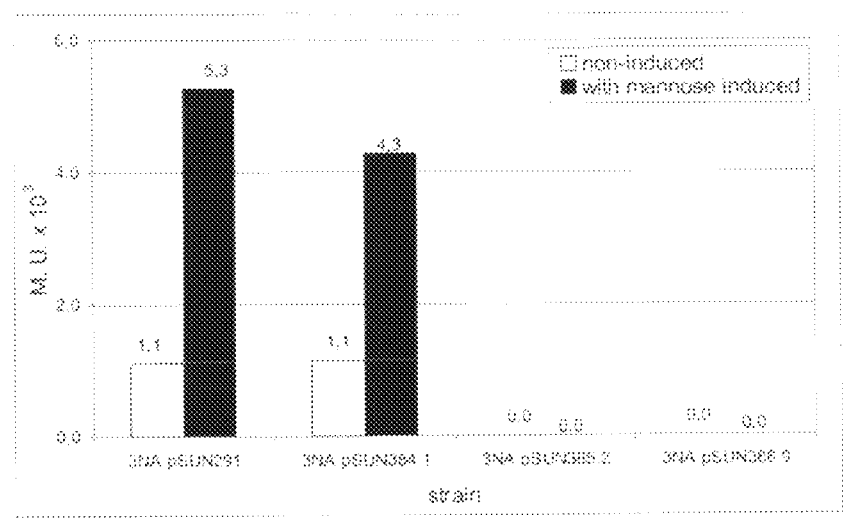
FIG. 10 the β-galactosidase activities of *B. subtilis* 3NA comprising the vectors pSUN291, pSUN385.2 and pSUN386.9 with the nucleic acid sequences as shown in FIG. 4.

The result is shown in FIG. 10. Here, the basal expression was already relatively high and was further increased by the 3-fold by addition of 0.2% mannose. Addition of glucose led to repression of β-galactosidase activity to nearly the basal expression level.

The result indicated that the manR promoter is not just a weak constitutive promoter but subject to mannose and CCR regulation.

c) Localization of manR Promoter Region

As in experiment 2c) for further localization of the promoter region of manR DNA-fragments of different lengths were prepared from the DNA-sequence as contained in pSUN291 by PCR amplifying DNA with primers binding at different positions upstream to the transcription initiation site of manR promoter (primer s5932 and s5933) and a primer binding downstream in the lacZ gene (s5934) (FIG. 4).

A first deletion sequence was obtained by shortening the sequence shown in FIG. 4 down to by −82 and by −81 upstream of the transcription inition site G and the second deletion was obtained by shortening down to by −62 and by −61 upstream of the transcription initiation site G.

Analogous to experiment 2c) the PCR fragments were digested with endoR SacI and NheI and ligated to pSUN279.2 DNA digested by the same restriction enzymes and the resulting plasmids named pSUN385.2 and pSUN386.9, respectively.

Each plasmid was inserted into *B. subtilis* 3NA and cultured as set out in experiment 2b. After one hour induction the β-galactosidase activity of the cells was determined as set out in experiment 2b. The results are shown in FIG. 10. There is no significant difference concerning induction of lacZ by mannose of *B. subtilis* 3NA comprising pSUN385.2 compared to pSUN291. However, in *B. subtilis* pSUN386.9 with the second deletion sequence, induction by mannose was completely abolished and the basal expression level was nearly 0. From this results follows that the ManR binding site of the manR promoter region is located between bp−81 and bp−35 with respect to the transcription initiation site of manR. The ManR binding site might even overlap the −35 sequence as it is found for classI activators since the inverted repeated sequence found in the proposed binding site extends into the proposed −35 sequence.

II) Construction of Recombinant Host Cell with Genetically Altered Gene Regions of Mannose Operon Experiment 4: Transformation a) Construction of Plasmid pMW168.1 as Expression Vector Using the nucleic acid sequence of the manP promoter region as introduced in plasmid pSUN284.1 as shown in FIG. 5 and as used in experiment 2c, plasmid pMW168.1 was constructed as set out below and introduced into *B. subtilis* 3NA as host.

A shuttle vector replicable in both *E. coli* and *B. subtilis* was designed as set out in Experiment 2a) with the exception that eGFP was used as reporter gene instead of lacZ. Also the transcription initiation region of manP was replaced by that of the gene gsiB (Stress protein; Jürgen et al., supra). Thereby also the start codon of eGFP and 6 codons following the start codon were replaced.

Figure 16:
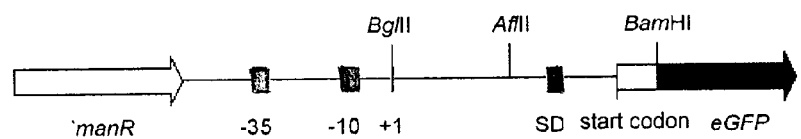
FIG. 16 the schematical structure of the obtained promoter and transcription initiation region of plasmid pMw168.1.

The schematical structure of the obtained promoter and transcription initiation region is shown in FIG. 16.

Shown is the arrangement of the genes (arrows) and the regions (boxes) with the relevant restriction sites.

Figure 15:
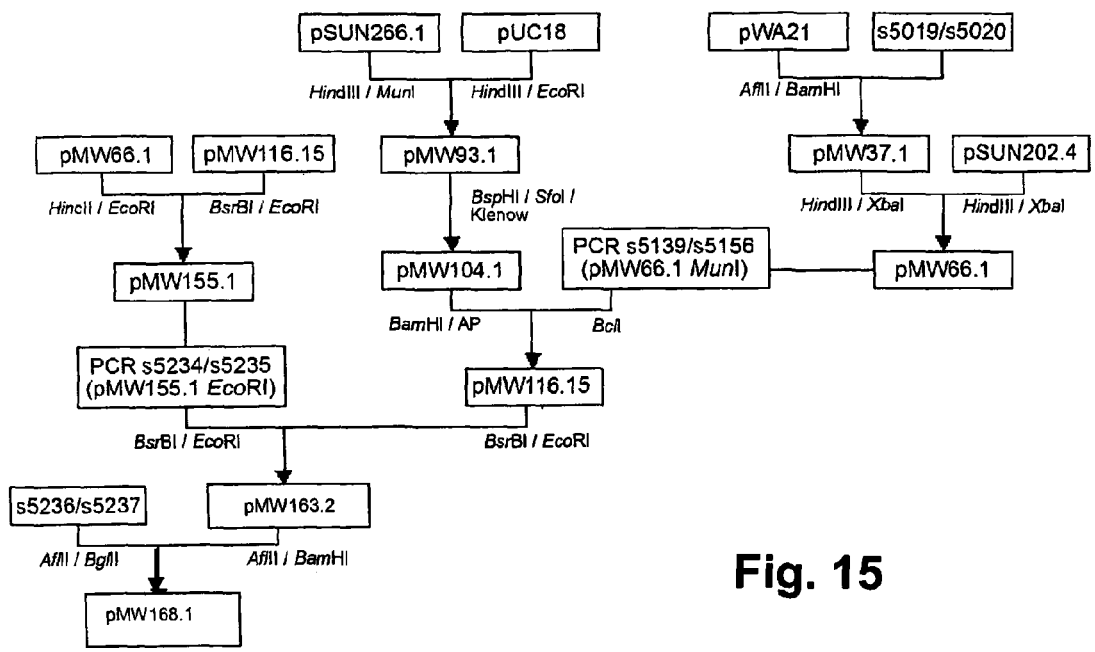

The sequence of the transcription initiation region gisB used was:

SEQ ID NO 43
5'-cttaagAATTAAAGGAGGAATTCAAAATGGCAGACAATAACAAAggatcc-3'
Af/II        SD    Startcodon        BamHI Generally, plasmid pMW168.1 was obtained as shown in the flow chart of FIG. 15.

In the flow chart the names of the vector-DNAs, the insert-DNAs and the complementary oligonucleotides used were as indicated in the boxes, with respect to the products of PCR the primers and the template-DNA were as within the brackets, the restriction enzymes used were indicated at the respective sites.

The cloning steps were carried out with *E. coli* JM109.

The plasmids used were pUC18, a cloning vector for PCR products with amp-resistance (Yanosch-Perron et al., supra); pWA21 an expression and cloning vector for *E. coli* with amp-resistance (Wegerer et al., 2008, BMC Biotechnol. 8, 2); pSUN202.4 a pUB110 derivate with manP promoter region and amp and kan resistance, being a shuttle vector for *E. coli* and *B. subtilis*; and pSUN266.1, a pUC18 derivate with integration site between ter-sequences and spc and amp resistance.

The plasmid pSUN266.1 is a derivative of rhamnose-inducible expression vector pWA21 where the rhamnose promoter and eGFP gene was replaced by a sequence containing two transcription terminators of the tufA gene of *Bacillus subtilis* in direct orientation and separated by restriction sites for BamHI, SmaI and AR (see sequence below) as well as a spectinomycin resistance gene. The later was amplified from plasmid pDG1730 (Cuerout-Fleury et al 1996) with the primers s4833 and s4835 (table 1). In the final construct pMW168 the mannose promoter and eGFP gene is inserted between the two tufA transcription terminator sequences.

mycin resistance gene. The spectinomycin resistance gene was amplified from pDG1730 (see above for pSUN266.1). The erythromycin resistance gene was amplified from plasmid pDG1730 by the primer s5069 and s5070. The C-terminal end of the manR gene was amplified from *Bacillus subtilis* DNA by the primer s5407 and s5408 and inserted on one side of the erythromycin gene. The N-terminal end of manA was amplified from the *Bacillus subtilis* chromosome by the primer s5362 and s5363 and inserted at the other side of the erythromycin resistance gene.

Figure 12:
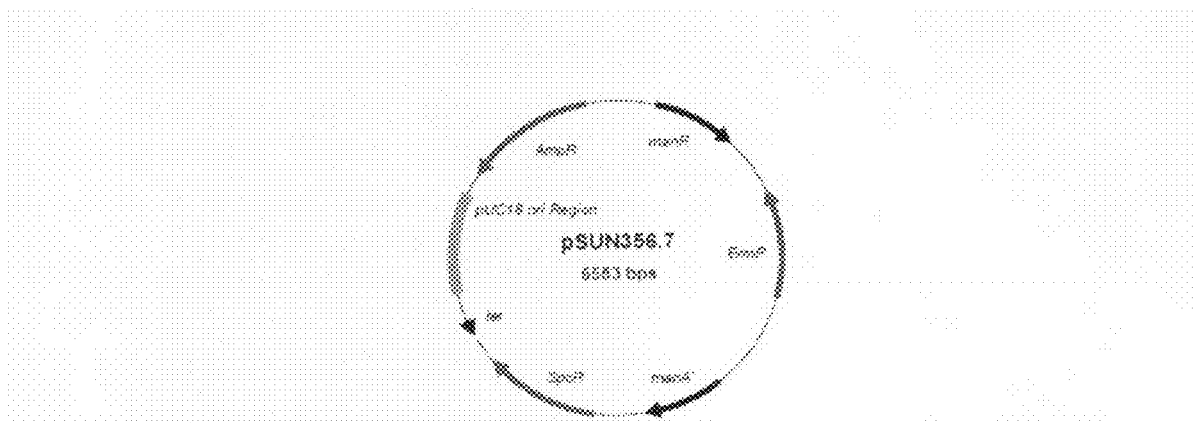
FIG. 12 the plasmid map of insertion vector pSUN356.7 (ΔmanP)

The map of plasmid pSUN356.7 is shown in FIG. 12.

b2) Deletion of manA

Further, a *B. subtilis* knockout mutant was produced with deleted manA from the mannose operon on the chromosome of sporulation deficient *B. subtilis* 3NA, with insertion vector pSUN281 resulting in *B. subtilis* TQ281 (spo0A3, manA::ermC) (see Sun T. et al, supra).

Gene manA encodes for mannose-6-phosphate isomerase which converts mannose-6-phosphate to fructose-6-phosphate.

For monitoring successful deletion an erythromycin resistance cassette was used.

b3) Transformation

*B. subtilis* TQ356 and *B. subtilis* TQ281 according to above b1) and b2) were each transformed with plasmid pMW168.1 obtained above in a1).

SEQ ID NO 44
BamHI SmaI AflII                           PmeI    HindIII
AATTGCGT*CGAGACCCCTGTGGGTCTCGTTTTTT*GGATCCCCGGGACGT*CGAGACCCCTGTGGGTCTCGTTTTTT*GTTTAAACAAGCTT SEQ ID NO 45
TTAACGCA*GCTCTGGGGACACCCAGAGCAAAAAA*CCTAGGGGCCCTGCA*GCTCTGGGGACACCCAGAGCAAAAAA*CAAATTTGTTCGAA Nucleotide sequence of the two tufA terminator sequences (bold, italics) and restriction sites between and at the end of the sequence (underlined).

Replacement of the transcription initiation region inclusive the start codon and the codons following the start codon were carried out using complementary oligonucleotides and via the single restriction sites BglII, AflII and BamHI. The construction of the vector started with the replacement of the transcription initiation region of the T7 gene 10 of vector pWA21 (Wegerer et al., supra) by the transcription initiation region of tufA from *B. subtilis* via complementary oligonucleotides s5019 and s5020, respectively. In further cloning steps this transcription initiation region was replaced by that of gsiB (Oligonucleotides s5236/s5237). The final plasmid pMW168.1 contained the rep gene inclusive ori+ from pUB110.

Figure 11:
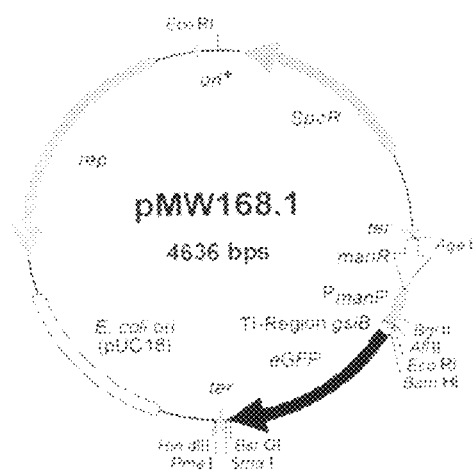
FIG. 11 the plasmid map of expression vector pMW168.1.

The plasmid map of pMW168.1 is shown in FIG. 11.

b) Deletion Mutant Strains Lacking manP (ΔmanP) and manA (ΔmanA)

b1) Insertion Vector for Deletion of manP

Insertion vector pSUN356.7 was used to delete gene manP encoding for the mannose-specific EII from the mannose-operon on the chromosome of sporulation deficient *B. subtilis* NA and the obtained strain was named *B. subtilis* TQ356 (spo0A manP::ermC). As selection marker erythromycin resistance cassette was used. Vector pSUN356.7 is a pUC18 derivate (ampicillin resistance) and contains an erythromycin resistance gene flanked by sequences of manR and manA and outside the replacement cassette a spectino- Media Used:

a) Minimal Glucose (MG):

| | |
|---|---|
| 2.0 g | $(NH_4)SO_4$ |
| 6.0 g | $KH_2PO_4$ |
| 14.0 g | $K_2HPO_4$ |
| 1.0 g | $Na_3Citrat$ |
| 0.2 g | $MgSO_4*7H_2O$ |
| 5.0 g | Glucose (separately as 20-50% stock solution) | b) Medium I:

| | |
|---|---|
| 9.50 ml | MG |
| 0.20 ml | Casaminoacids (1% stock solution) |
| 0.05 ml | $MgSO_4$ (1M stock solution) | c) Medium II:

| | |
|---|---|
| 8.00 ml | MG |
| 0.10 ml | Casaminoacids (1% stock solution) |
| 0.05 ml | $MgSO_4$ (1M stock solution) |

Transformation was carried out following the protocol of Anagnostopulos et al, "Requirements for transformation in *Bacillus subtilis*" J. Bacteriol. (1961) 81: 741-746. A single colony of each bacterial strain was given to 5 ml medium I and incubated at 37° C. in a roller overnight. 1 ml of the overnight culture ($OD_{600}$ between 1 and 2) was transferred into 8 ml medium II in a 100 ml baffled Erlenmeyer flask and incubated at 37° C. for 85 min. Then, 1 ml of competent cells were transferred into testtubes of Schütt Company and mixed with the respective insertion vectors. Prior to admixing with the competent cells the insertion vectors had been cut at a non essential site with a single cutter. The obtained mixture was precipitated by isopropanol and allowed to ligate at room temperature for at least 2 hours.

Then, the obtained transformed cells were incubated at 37° C. for 30 min in a roller, centrifuged at 4,500 rpm for 5 min at room temperature. The pellet was resuspended in residual liquid and plated.

Experiment 5: Fermentation 5.1 Materials and Methods

In general, also for the fermentation experiments standard molecular techniques were used if not stated otherwise.

Composition of Media Used for Fermentation

Overnight culture and preculture #1 were carried out in Spizizen's minimal salts medium (SMM) (Spizizen J., Proc. Natl. Acad. Sci. U.S.A. 44, 1958, 1072-1078), supplemented with 0.02% (w/v) Casamino acids (BD Difco™, Sparks, Md., USA) as well as 100 µg $mL^{-1}$ spectinomycin for plasmid selection and 5 µg $mL^{-1}$ erythromycin for strain selection (in case of TQ281 and TQ356). Preculture #2 and fermentation culture (batch) were carried out using a mineral medium modified from Wilms et al. (Wilms B. et. al., Biotechnol. Bioeng. 73, 2001, 95-103) consisting of: 1.0 g $L^{-1}$ $(NH_4)_2$—H-citrate, 2.0 g $Na_2SO_4$, 2.68 g $NH_4SO_4$, 0.5 g $NH_4Cl$, 14.6 g $K_2HPO_4$, 4.0 g $Na_2HPO_4 \times 2H_2O$, 1.0 g $L^{-1}$ $MgSO_4 \times 7H_2O$, 3 mL $L^{-1}$ trace element solution (TES), 5 g $L^{-1}$ glucose for the preculture #2 and 25 g $L^{-1}$ glucose for the batch medium. TES contains 0.5 g $CaCl_2$, 0.18 g $L^{-1}$ $ZnSO_4 \times 7H_2O$, 0.1 g $MnSO_4 \times H_2O$, 10.05 g $L^{-1}$ $Na_2$-EDTA, 8.35 g $L^{-1}$ $FeCl_3$, 0.16 g $L^{-1}$ $CuSO_4 \times 5H_2O$, and 0.18 g $L^{-1}$ $CoCl_2 \times 6H_2O$. The feed medium for high-cell-density fermentations contained 200 g $L^{-1}$ glucose, 7.89 g $L^{-1}$ $MgSO_4 \times 7H_2O$, 40 mL $L^{-1}$ of TES, and 63.36 g $L^{-1}$ $(NH_4)_2HPO_4$ when a KLF reactor was used. The pH was adjusted to 3.3 to assure the solubility of all components. Two separate feed media were used when a 30 $L^{-1}$ reactor was used. The first medium contained 654.76 g $L^{-1}$ glucose×$H_2O$, 23.5 g $L^{-1}$ $MgSO_4 \times 7H_2O$, 120 mL $L^{-1}$ of TES, the second 396 g $L^{-1}$ $(NH_4)_2HPO_4$. For induction of the manP promoter, either 20% (w/v) D-mannose solution or a separate feeding solution containing 200 g mannose, 7.89 g $L^{-1}$ $MgSO_4 \times 7H_2O$, 40 mL $L^{-1}$ of TES, and 63.36 g $L^{-1}$ $(NH_4)_2HPO_4$ was used.

Preculture and Fed-Batch Cultivation Conditions

Single colonies from LB agar plates were inoculated in 5 mL of SMM and incubated overnight for at least 14 h at 37° C. 25 mL of SMM were transferred to 250-mL shaking flasks and inoculated with the overnight culture to achieve an optical density of 0.05 (preculture #1) at 600 nm ($OD_{600}$). After 5 h of incubation at 37° C., 20 mL of preculture #1 were used to inoculate 200 mL of preculture #2 medium in 1000-mL shaking flasks (preculture #2). After another 7 h of incubation at 37° C., the batch culture medium was inoculated with preculture #2.

A fed-batch fermentation setup previously developed and optimized for *E. coli* with glucose as the main carbon source (Korz D. J. et al., J. Bacteriol. 39, 1995, 59-65; Wilms supra) was used. The batch volume was 1.5 L when a 3.7-liter Small Laboratory Fermenter KLF (Bioengineering AG, Wald, Switzerland) was used and the feeding volume 1.0 L. In the case of a 30-liter Laboratory Fermenter D598 (LF; Bioengineering AG, Wald, Switzerland) the batch volume was 8.0 L, the glucose feed medium 4.2 L and the ammonia feed medium 1.0 L. Glucose and ammonia media were fed into the reactor in a 81%:19% ratio. The feed media were fed into the bioreactor according to:

$$F(t) = [(\mu_{set}/Y_{X/S}) + m] \times [(c_{x0} \times V_0)/c_{s0}] \times \exp(\mu_{set} \times t) \quad \text{Eq. 1}$$

where F (L $h^{-1}$) is the feeding rate, $\mu_{set}$ ($h^{-1}$) is the desired specific growth rate, m (g $g^{-1}$ $h^{-1}$) is the specific maintenance coefficient (=0.04 $g^{-1}$ $h^{-1}$), $Y_{x/s}$ is the specific biomass/substrate yield coefficient (approximately 0.5 for glucose), $c_{x0}$ (g $L^{-1}$) is the biomass concentration at start of feeding, $V_0$ (L) is the reactor volume at start of feeding, $c_{s0}$ (g $L^{-1}$) is the glucose concentration in the feeding solution, and t (h) is the time after start of feeding. A specific growth rate p of 0.1 $h^{-1}$ was chosen to avoid the production of nonspecific and unwanted byproducts and to avoid oxygen limitation.

The batch was carried out at 37° C. until the temperature was shifted to 30° C. with the beginning of the fed-batch phase to avoid unwanted inclusion body formation of the expressed heterologous protein. The pH was adjusted to 7.0 with 24% (v/v) $NH_4OH$ and 20% (v/v) $H_3PO_4$, respectively. The $pO_2$ value was maintained over 50% saturation by an automatically adjusting stirrer speed. The aeration rate was kept constant at 2 L $min^{-1}$ when using the KLF and between 15-25 L $min^{-1}$ when using the LF. The overpressure was kept at 0.5 bar. The cell density was determined by measuring the $OD_{600}$ periodically with the Ultrospec™ 1100 pro UV/visible spectrophotometer (GE Healthcare, formerly Amersham Biosciences, United Kingdom). The cell dry weight (cdw) was calculated by multiplying the $OD_{600}$ value with the factor of 0.322 $g_{cdw}$ $L^{-1}$, which was obtained as an average value after several moisture determinations with the MB 835 Halogen (Ohaus Corporation, Pine Brook, N.J., USA) during the fermentations. The Biolog 1.7 software package (Institute of Biochemical Engineering, University of Stuttgart, Germany [http://www.ibvt.uni-stuttgart.de]) was used for controlling the fermentation parameters. The fed-batch fermentations were terminated after approximately 40 h of process time.

Online and Offline Fluorescence Measurements

To track the expression rate of the produced recombinant eGFP in real time, a fluorescence probe (Mikropack HPX-2000, High Power Xenon Lightsource; Ocean Optics, Inc.; S2000 fibre optic spectrometer; Dunedin, Fla., USA) was used inside the bioreactor. The extinction wavelength was 485 nm whereas the emission was detected at 535 nm and recorded online by the SPECTRA SUITE® software package (Ocean Optics, Dunedin, Fla. USA). The fluorescence light was channeled through an optic filter with a strength of 0.6. The integration time of the probe was 50 msec. Because of the fact that the software was only able to count values up to 4,000 counts the integration time was reduced stepwise right before reaching higher levels. Hence the fluorescence counts were multiplied afterwards with the corresponding reduction factor to get the values which correspond to 50 msec. The measured values were specific for a certain reactor volume.

Additionally, offline measurements of fluorescent activity were conducted by using the SpectraFluor Microplate Reader (Tecan Group Ltd., Mannedorf, Switzerland). Therefore 3×250 µl of undiluted cell culture were measured in 96-well microplates (Greiner-Bio One GmbH, Frickenhausen, Germany) using 3×250 µl batch medium as blank value (Excitation Filter: 485 nm; Emission Filter: 535 nm; Gain (manual): 60; Integration time: 20 µsec; Number of flashes: 3; Read mode: Top). The average of the blank values was substracted from the average of the samples to get the final value. Cell culture was diluted in batch medium as soon as reaching 20,000 counts.

From a calibration against an internal purified eGFP standard (approx. 95% purity, 1.3 g $L^{-1}$) it could be conveyed that about 120,000 offline measured counts correspond to 1 $g_{eGFP}$ $L^{-1}$. It could be shown that a linear coherence exists between the offline and online measured values which gave a correlation of 1.5 $g_{eGFP}$ $L^{-1}$ per 7470 online measured counts.

Determination of Plasmid Stability

The stability of vector pMW168.1 was determined by measuring the fraction of plasmid-containing cells according to Harwood and Cutting (Harwood C. R. et al, Molecular Biological Methods for *Bacillus*, 1990, John Wiley & Sons Ltd., Chichester, England.

Protein Analysis by SDS-PAGE

Crude cell extracts were obtained as follows: $10^{10}$ cells were harvested and centrifuged. The pelleted cells were resuspended with 1 mL 50 mM sodium phosphate buffer (pH 7.5) and solubilised using ultrasonic sound (Heat Systems-Ultrasonics, Inc., model W-385 sonicator, Farmingdale, N.Y., USA; 3×30 sec, 50% duty cycle). The soluble protein fraction was obtained from the supernatant after centrifugation, the insoluble fraction was obtained by resuspending the pellet with 1 mL 50 mM sodium phosphate buffer (pH 7.5). The protein fractions were analyzed by SDS-PAGE (Laemmli U.K., Nature 227, 1970, 680-685; LeBlanc D. J. et al., Antimicrob. Agents Chemother 35, 1991, 1804-1810).

5.2 High-cell-density fermentations using *B. subtilis* 3NA/pMW168.1.

The mannose expression system with *B. subtilis* 3NA/pMW168.1 was tested in fed-batch fermentations. A setup was used as described previously (Korz et al., Wilms et al., supra).

In the first fermentation, carried out in a LF stirring reactor, a bonus of 0.2% (w/v) D-mannose was added to the culture broth immediately with the beginning of the fed-batch phase. The fluorescence signal of the probe showing no significant fluorescence so far, increased very quickly right after induction. After reaching a peak value at about 2,200 counts after 4 h in the fed-batch phase, the signal began to decrease again steadily. This decrease was accompanied by the consumption of inducer (measured by HPLC, data not shown). At the end of the process 0.2 $g_{eGFP}$ $L^{-1}$ or 3 $mg_{eGFP}$ per $g_{cdw}$ were produced.

In a second fermentation, an additional exponential D-mannose feed was used. That was started simultaneously with the glucose feed keeping the overall sugar concentration of both feeds as high as in the first fermentation. The fluorescence signal started right after the addition of inducer and was extended until the end of the process. An overall amount of 50 g D-mannose was added to the reactor broth to sustain this increase. With this induction regime 2.1 $g_{eGFP}$ $L^{-1}$ or 53 $mg_{eGFP}$ per $g_{cdw}$ were produced. The detailed results of the two fermentations conducted with *B. subtilis* 3NA/pMW168.1 are summarized in the table shown in 5.5 Results.

The eGFP production increased throughout the whole fed-phase but slower than the biomass production. A plasmid stability check revealed that about 95% of the cells were still carrying the vector at the end of both fermentation processes.

5.3 High-Cell-Density Fermentation Using the ΔmanA Strain TQ281.

The manA deletion strain TQ281 incapable of growing on mannose as the sole carbon source (Sun T. et al., supra) was chosen for further fermentation experiments. *B. subtilis* TQ281 transformed with pMW168.1 showed a sensitivity against D-mannose in shaking flask experiments.

Two fed-batch fermentations were set up with TQ281/pMW168.1. In the first one, induction took place by a single addition of mannose with the beginning of the fed-batch phase. In the second one, an additional exponential mannose feed was started at the same time. Induction with D-mannose showed no significant impact on the specific growth rate in the fed-batch phase. With the single addition strategy 0.71 $g_{eGFP}$ $L^{-1}$ corresponding to 36 $mg_{eGFP}$ per $g_{cdw}$ could be achieved, with the exponential feeding strategy 1.9 $g_{eGFP}$ $L^{-1}$ corresponding to 32 $mg_{eGFP}$ per $g_{cdw}$. The detailed results of the two fermentations are listed in Table of 5.5 Results.

5.4 Development and Application of an Autoinducible Expression System in High-Cell-Density Fermentation Using the ΔmanP Strain TQ356.

The *B. subtilis* ΔmanP strain TQ356 showed a constitutive expression under non-inducive conditions from $P_{manP}$ as well as an CCR effect when glucose was present (Sun T. et al., supra). That strain was transformed with pMW168.1 which led to rather small fluorescing colonies. After addition of 0.5% (w/v) glucose to the selection media, colony growth was normalized. In shaking flask experiments high expression levels were achieved, when glucose got exhausted (data not shown).

Figure 13:
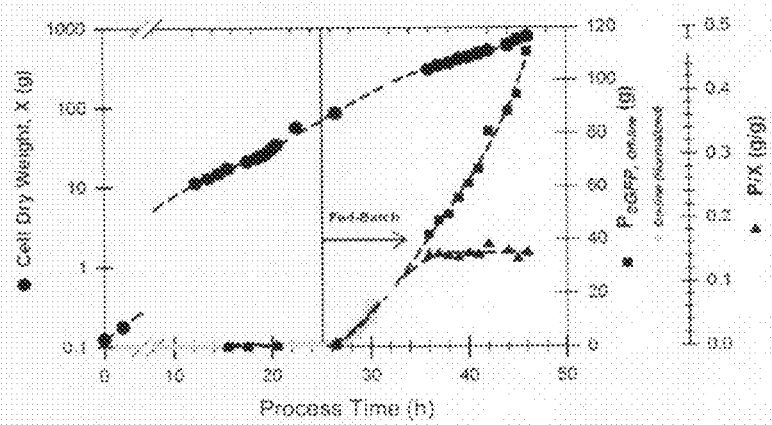
FIG. 13 a diagram showing logarithmically the dry biomass concentration plotted over the process period of the fermentation of *B. subtilis* TQ356/pMW168.1 (ΔmanP-mutant) and the fluorescence signal (RFU) plotted over the process period.
Figure 14:
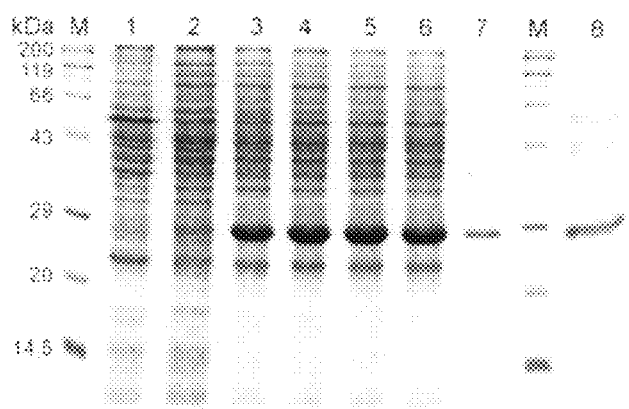
FIG. 14 the SDS-PAGE of cell samples taken from the fermentation with *B. subtilis* TQ356/pMW168.1, and FIG. 15 a flow chart with preparation of plasmid pMw168.1.

*B. subtilis* TQ356 harbouring pMW168.1 was then used for a fed-batch fermentation (FIG. 13). In the batch phase no significant fluorescence could be detected similar to the batch fermentation of *B. subtilis* strains 3NA/pMW186 and TQ281/pMW168. With the beginning of the fed-batch phase the fluorescence signal of the reactor probe began to increase continuously. After 36 h overall fermentation time the expression level in the cells reached a maximum, as it can be seen by a constant $Yp_{P/X}$ value of 14.6% until the end of the fermentation process, which corresponds to a constant specific productivity. Nearly 10 $g_{eGFP}$ $L^{-1}$ corresponding to 146 mg of eGFP per $g_{cdw}$ were produced without any addition of inducer. The fermentation results are summarized and compared to the other conducted fermentations in the table set out below in 5.5 Results. A SDS-PAGE was conducted to get an impression about the percentage of expressed eGFP in comparison to total protein (FIG. 14). As it can be seen at least 20% of total protein are eGFP molecules. Only a small fraction is insoluble and present in the form of inclusion bodies (FIG. 14, lane 7). Undiluted culture broth supernatant was also analysed by SDS-PAGE (FIG. 14, lane 8) and measured spectrophotometrically. About 1% of the total measured eGFP was found in the supernatant which might be due to ongoing cell lysis throughout the fermentation process.

Plasmid stability and cell morphology were checked throughout the fermentation process.

5.5 Results

The results of the fermentation runs of 5.2 to 5.4 are summarized in the table below.

Comparison of conducted fermentations with regard to the different induction regimes and used *B. subtilis* strains with expression vector pMW168.1. b

| B. subtilis strain with pMW168.1 | induction regime | stirring reactor | $\Delta t_{fb}$ [h] | $C_{x,final}$ [$g_{cdw}$ L$^{-1}$] | $X_{final}$ [$g_{cdw}$] | $C_{P,final}$ [$g_{eGFP}$ L$^{-1}$] | $P_{eGFP,final}$ [g] | $Y_{P/X}$ [%] | $r_p$ [$g_{eGFP}$ $g_{cdw}^{-1}$ h$^{-1}$] | $q_P$ [$g_{eGFP}$ L$^{-1}$ h$^{-1}$] |
|---|---|---|---|---|---|---|---|---|---|---|
| 3NA (man⁺) | SA | LF | 22.5 | 73 | 897 | 0.2 | 2.8 | 0.3 | 0.14 × 10$^{-3}$ | 0.01 |
| 3NA (man⁺) | EF | KLF | 23.8 | 39 | 103 | 2.1 | 5.5 | 5.3 | 2.32 × 10$^{-3}$ | 0.09 |
| TQ281 (ΔmanA) | SA | KLF | 11.8 | 20 | 39 | 0.7 | 1.4 | 3.6 | 2.98 × 10$^{-3}$ | 0.06 |
| TQ281 (ΔmanA) | EF | LF | 25.5 | 59 | 782 | 1.9 | 25 | 3.2 | 1.37 × 10$^{-3}$ | 0.08 |
| TQ356 (ΔmanP) | AI | LF | 23.5 | 67 | 758 | 9.8 | 111 | 14.6 | 6.23 × 10$^{-3}$ | 0.40 | b abbreviations and parameter discriptions:
SA: single addition of inducer (mannose);
EF: exponential feeding of inducer (mannose);
AI: autoinduction;
final: at the end of the fermentation process;
LF: 30-liter Laboratory Fermenter;
KLF: 3.7- liter Small Laboratory Fermenter;
$\Delta t_{fb}$: fed-batch time/duration,
$_{final}$: at the end of the fermentation;
$c_{x,final}$: cell dry weight concentration;
$X_{final}$: absolute cell dry weight;
$C_{p,final}$: product concentration;
$P_{eGFP,final}$: absolute product (eGFP);
$Y_{P/X}$: product per g cell dry weight;
$r_P$: specific productivity,
$q_P$: volumetric productivity.

As shown by these results during the batch phase virtually no expression of the reporter eGFP took place. In the auto-inducible fermentation of 5.4 the initiation of autoinduction at the beginning of the glucose-restricted transition phase between the batch and fed-batch phase of fermentation, and its maintenance throughout the interior glucose-limiting fed-batch phase led to a threefold increase of product yield to 146 mg GPF per gcdw.

Further as shown by the results obtained with TQ281 (fermentation 5.3) the yield obtaind by single addition of inducer of 0.7 g (eGFP)/L can be significantly increased by additional feeding of inducer during the exponential phase to 1.9 g/L.

5.6 Discussion

In fermentations 5.2 to 5.4 B. subtilis expression systems were used comprising the mannose promoter PmanP in the vector pMW 168.1 to promote expression of eGFP. The promoter PmanP has proven to be a strong promoter which is activated upon the addition of D-Mannose.

In fermentation 5.2 the B. subtilis sporulation-deficient strain 3NA, which was transformed with this vector, led to high product levels, i.e. 2.1 $g_{eGFP}$ L$^{-1}$. Compared to a recently described system with B. megaterium (Stammen et al., Appl. Environ. Microbiol. 76, 2010, 4037-4046), a promising host system for recombinant protein production, the B. subtilis system leads to superior results. The intracellular B. megaterium protein production system, which is inducible by xylose, gave 1.25 $g_{GPF}$L$^{-1}$, corresponding to 36.8 mg per $g_{cdw}$ in fed-batch fermentations. In addition, Stammen et al. (supra) used antibiotics until the end of the fermentation process, with the result that no plasmids were lost during the fermentation process.

Fermentation 5.2 shows that the mannose system is rather efficient concerning the productivities, however a one-time addition of the inducer does not lead to permanent high expression rates. This is due to the rapid consumption of the inducer mannose as it is one of the favourite carbon sources of B. subtilis.

Thus, the present application relates to a method for producing a heterologous polypeptide in a sporulation-deficient B. subtilis host cell, comprising the step of transfection the sporulation-deficient B. subtilis cell with a vector containing the manP promoter operably linked to the nucleotide sequence encoding the polypeptide, growing the transformed host cell in a medium under suitable conditions for allowing expression of said polypeptide and recovering the polypeptide from the cell or from the cell culture, whereby the expression of the polypeptide is induced by the addition of the inducer mannose. In a preferred embodiment of the present application the inducer mannose is added at the beginning of the fed-batch phase. In another preferred embodiment the inducer mannose is added first at the beginning of the fed-batch phase and a second addition of mannose is effected during exponential growth simultaneously with the glucose feed.

An expression system with reduced inducer requirement was achieved by fermentation 5.3 by disrupting the mannose 6-phosphate isomerase gene manA. This leads to a system wherein less inducer was needed to obtain high expression rates as could be observed in shaking flask experiments.

However, that system was accompanied by a self-toxification of the cells since growth was inhibited when using amounts over 0.5% (w/v) mannose. That effect may be due to the intracellular accumulation of mannose 6-phosphate. Another possible reason for the sensitivity of the ΔmanA strain TQ281 against mannose may be the strong reduction of available phosphate groups, since phosphate is irreversibly bound to mannose when entering the cells via the PTS.

Thus, the present application relates to a method for producing a heterologous polypeptide in a B. subtilis host cell deficient in the manA gene, comprising the step of transfection the B. subtilis cell deficient in the manA gene with a vector containing the manP promoter operably linked to the nucleotide sequence encoding the polypeptide, growing the transformed host cell in a medium under suitable conditions for allowing expression of said polypeptide and recovering the polypeptide from the cell or from the cell culture, whereby the expression of the polypeptide is induced by the addition of the inducer mannose in an amount not exceeding 0.5% (w/v). In a preferred embodiment of the present application the inducer mannose is added at the beginning of the fed-batch phase. In another preferred embodiment the inducer mannose is added first at the beginning of the fed-batch phase and a second addition of mannose is effected during exponential growth simultaneously with the glucose feed.

An induction regime which does no longer need any inducer is shown in Example 5.4. That autoinducible system was put into effect with the ΔmanP strain TQ356 and expression vector pMW168.1.

In a transporter negative strain like TQ356 the mannose promoter is only under regulatory control by the CCR committed by glucose which is e.g. the case in the batch phase of a fermentation process. The negative regulatory effect by the cognate transporter ManP is abolished. Nevertheless, the regulator stays in an inactive state as long as glucose is present. In addition, there are not sufficient amounts of ManR since the manR operator site is blocked. Not until glucose becomes limiting ManR can bind to its operator sequence and start the expression. That autoinduction system rendered the need for the rather expensive inducer unnecessary. This sophisticated induction strategy is very promising for industrial applications, since no significant unwanted basal expression takes place in the batch phase and no addition of any inducer is necessary to get high expression levels throughout the fed-batch phase.

Beyond that also relative high expression rates combined with high productivities compared to fermentations 5.2 and 5.3 could be obtained. Nearly 10 g $L^{-1}$ of recombinant protein (eGFP) corresponding to 146 $mg_{eGFP}$ per $g_{cdw}$ could be produced. The product was homogeneously distributed in the cells due to its solubility as it could be observed by fluorescence microscopy and SDS-PAGE analysis. The high expression rate, i.e high the productivity could be maintained at a constant high level until the end of the fermentation process.

Thus, the present application also relates to a method for producing a heterologous polypeptide in a transporter negative *B. subtilis* host cell such as a cell deficient in the manP gene, comprising the step of transfection the transporter negative *B. subtilis* cell with a vector containing the manP promoter operably linked to the nucleotide sequence encoding the polypeptide, growing the transformed host cell in a medium under suitable conditions for allowing expression of said polypeptide and recovering the polypeptide from the cell or from the cell culture, whereby the expression of the polypeptide is not induced by mannose but is under control of glucose.

---

The invention claimed is:

1. A method for producing a heterologous polypeptide in a recombinant bacterial host cell, which is subject to carbon catabolite repression and a phosphoenolpyruvate: carbohydrate phosphotransferase system and which is genetically altered such, that it is incapable of deactivating a transcriptional regulator protein ManR specific for a promoter inducible by a secondary carbon source mannose and which comprises a vector with a heterologous nucleic acid sequence encoding a polypeptide operably linked to the mannose-inducible promoter, said method comprising the steps of growing the bacterial host cell in a cell culture medium containing only a primary carbon source glucose but not the inducer mannose, whereby the expression of said polypeptide is not induced by mannose but by allowing the concentration of glucose to decrease during the duration of the a cell culture below a level that causes carbon catabolite repression, and recovering the polypeptide from the bacterial host cell or from the cell culture medium.

2. The method according to claim 1, wherein a bacterial host cell is used, in which by genetical alteration of the genome of the bacterial host cell, deactivation of ManR by phosphoryl groups transfer from enzyme EII ManP, specific for to ManR, is prevented, i) by deleting a gene encoding enzyme EII ManP from the bacterial host cell, or ii) by genetically altering in the genome of the bacterial host cell the gene encoding for ManR so that ManR expressed by said gene is unable to bind a phosphoryl group transferred from enzyme EII ManP to ManR.

3. The method according to claim 2 wherein in case i) into the vector is integrated the gene encoding for ManR controlling the promoter of the vector; or wherein ii) into the vector is integrated the genetically manipulated gene of the bacterial host cell encoding for ManR which is unable to bind the phosphoryl group transferred from the enzyme EII ManP to ManR.

4. The method according to claim 1, wherein the bacterial host cell is selected from *Bacilli, Clostridia* and *Escherichia*.

5. The method according to claim 1, wherein the cell culture medium comprises casamino acids.

6. The method according to claim 1, wherein glucose is added to the culture in an amount sufficient to maintain a pre-determined growth rate of the bacterial host cell without induction of carbon catabolite repression.

7. The method according to claim 1, wherein the mannose-inducible promoter is a promoter of the mannose operon.

8. The method according to claim 7, wherein the promoter is a PmanP or a PmanR promoter of the mannose operon.

9. The method of claim 1, wherein the bacterial host cell is *Bacillus*.

10. A recombinant bacterial host cell which is subject to carbon catabolite repression and the phosphoenolpyruvate: carbohydrate phosphotransferase system, and wherein the bacterial host cell is genetically altered such, that the bacterial host cell is incapable of deactivating a transcriptional regulator protein ManR specific for a promoter inducible by mannose in the absence of mannose by deleting, in the genome of the bacterial host cell, a gene which encodes a phosphoryl phosphoryl group transferring enzyme EII ManP specific for the transcriptional regulator protein ManR, and wherein the recombinant bacterial host cell comprises a vector with a heterologous nucleic acid sequence encoding a polypeptide operably linked to a promoter, wherein the promoter is regulated by the transcriptional regulator protein ManR, and wherein into the vector is integrated a gene encoding for the transcriptional regulator protein ManR, and wherein the expression of the heterologous nucleic acid sequence is independent of mannose.

11. A recombinant bacterial host cell, which is subject to carbon catabolite repression and the phosphoenolpyruvate: carbohydrate phosphotransferase system, and wherein the bacterial host cell is genetically altered such that the bacterial host cell is incapable of deactivating a transcriptional regulator protein ManR specific for a promoter inducible by mannose in the absence of mannose by genetically altering a gene encoding the transcriptional regulator protein ManR so that the transcriptional regulator protein ManR expressed by said genetically altered gene is incapable of binding a phosphoryl group transferred by enzyme EII ManP to ManR, specific for said transcriptional regulator protein ManR, and wherein the recombinant bacterial host cell comprises a vector with a heterologous nucleic acid sequence encoding a polypeptide operably linked to a promoter regulated by the transcriptional regulator protein ManR, and wherein into the vector is additionally integrated the genetically altered gene encoding for the transcriptional regulator protein ManR incapable of binding a phosphoryl group transferred from the enzyme EII ManP, and wherein the expression of the heterologous nucleic acid sequence is independent of mannose.

12. A recombinant bacterial host cell according to claim 10, wherein the bacterial host cell is selected from *Bacilli, Clostridia* and *Escherichia*.

13. A recombinant bacterial host cell according to claim 11, wherein the bacterial host cell is selected from *Bacilli, Clostridia* and *Escherichia*.

* * * * *

SEQUENCE LISTING

```
<160> NUMBER OF SEQ ID NOS: 45

<210> SEQ ID NO 1
<211> LENGTH: 143
<212> TYPE: DNA
<213> ORGANISM: Bacillus subtilis

<400> SEQUENCE: 1
tagggaaaaa tgcctttatt accggaacct atggtaaaaa aagcgatttt aatgagctga      60
tttcggtata cagttgagac aagatcttat tattcacact ttctagaaat aattttctta     120
agaaggagat atacatatga cac                                              143

<210> SEQ ID NO 2
<211> LENGTH: 80
<212> TYPE: DNA
<213> ORGANISM: Bacillus subtilis

<400> SEQUENCE: 2
tagggaaaaa tgcctttatt accggaacct atggtaaaaa aagcgatttt aatgagctga      60
tttcggtata cagttgagac                                                   80

<210> SEQ ID NO 3
<211> LENGTH: 195
<212> TYPE: DNA
<213> ORGANISM: Bacillus subtilis

<400> SEQUENCE: 3
tgaatttctg ctgaatatac attacatagc aaactcaaag agtataaaaa tcgcttttt       60 ccggaagctt cggtaaaaaa cgaaactttt gtctctatga ttttgtttta taatgtaaac     120
ggtttcttat atagtatact tatactatca atttgctcaa gtagatactg acaggcttaa     180
gaaggagata tacat                                                       195

<210> SEQ ID NO 4
<211> LENGTH: 128
<212> TYPE: DNA
<213> ORGANISM: Bacillus subtilis

<400> SEQUENCE: 4
```

-continued

```
tgaatttctg ctgaatatac attacatagc aaactcaaag agtataaaaa tcgcttttt       60 ccggaagctt cggtaaaaaa cgaaactttt gtctctatga ttttgtttta taatgtaaac     120
ggtttctt                                                              128

<210> SEQ ID NO 5
<211> LENGTH: 121
<212> TYPE: DNA
<213> ORGANISM: Bacillus subtilis

<400> SEQUENCE: 5
tgaatttctg ctgaatatac attacatagc aaactcaaag agtataaaaa tcgcttttt       60 ccggaagctt cggtaaaaaa cgaaactttt gtctctatga ttttgtttta taatgtaaac     120
g                                                                     121

<210> SEQ ID NO 6
<211> LENGTH: 41
<212> TYPE: DNA
<213> ORGANISM: Bacillus subtilis

<400> SEQUENCE: 6
aaaaaaacgc gtgtttaaac tgaatttctg ctgaatatac a                          41

<210> SEQ ID NO 7
<211> LENGTH: 34
<212> TYPE: DNA
<213> ORGANISM: artificial
<220> FEATURE:
<223> OTHER INFORMATION: primer s4694

<400> SEQUENCE: 7
aaaaaatcta gaaagtgtga ataataagat cttg                                  34

<210> SEQ ID NO 8
<211> LENGTH: 41
<212> TYPE: DNA
<213> ORGANISM: artificial
<220> FEATURE:
<223> OTHER INFORMATION: primer s4802

<400> SEQUENCE: 8
aaaaaaacta gtgtttaaac agggaaaaat gcctttatta c                          41

<210> SEQ ID NO 9
<211> LENGTH: 31
<212> TYPE: DNA
<213> ORGANISM: artificial
<220> FEATURE:
<223> OTHER INFORMATION: primer s4833

<400> SEQUENCE: 9
aaaaaagttt aaaccctgg cgaatggcga t                                      31

<210> SEQ ID NO 10
<211> LENGTH: 35
<212> TYPE: DNA
<213> ORGANISM: artificial
<220> FEATURE:
<223> OTHER INFORMATION: primer s4835

<400> SEQUENCE: 10
aaaaaagaat tcattagaat gaatatttcc caaat                                 35
```

-continued

```
<210> SEQ ID NO 11
<211> LENGTH: 59
<212> TYPE: DNA
<213> ORGANISM: artificial
<220> FEATURE:
<223> OTHER INFORMATION: primer s4956

<400> SEQUENCE: 11
aattgcgtcg agacccctgt gggtctcgtt ttttggatcc ggcgcccacg tggctagcc      59

<210> SEQ ID NO 12
<211> LENGTH: 59
<212> TYPE: DNA
<213> ORGANISM: artificial
<220> FEATURE:
<223> OTHER INFORMATION: primer s4957

<400> SEQUENCE: 12
ttaaggctag ccacgtgggc gccggatcca aaaaacgaga cccacagggg tctcgacgc      59

<210> SEQ ID NO 13
<211> LENGTH: 30
<212> TYPE: DNA
<213> ORGANISM: artificial
<220> FEATURE:
<223> OTHER INFORMATION: primer s5006
<220> FEATURE:
<221> NAME/KEY: misc_feature
<222> LOCATION: (1)..(1)
<223> OTHER INFORMATION: Cy labeled

<400> SEQUENCE: 13
tagccttttt tatagttgtt cagccactgt                                      30

<210> SEQ ID NO 14
<211> LENGTH: 30
<212> TYPE: DNA
<213> ORGANISM: artificial
<220> FEATURE:
<223> OTHER INFORMATION: primer s5007
<220> FEATURE:
<221> NAME/KEY: misc_feature
<222> LOCATION: (1)..(1)
<223> OTHER INFORMATION: cy labeled

<400> SEQUENCE: 14
atccacgcca taatgcatgc cgccattaat                                      30

<210> SEQ ID NO 15
<211> LENGTH: 44
<212> TYPE: DNA
<213> ORGANISM: artificial
<220> FEATURE:
<223> OTHER INFORMATION: primer s5019

<400> SEQUENCE: 15
ttaagctctt aaggaggatt ttagaatggc taaagaaaaa ttcg                      44

<210> SEQ ID NO 16
<211> LENGTH: 44
<212> TYPE: DNA
<213> ORGANISM: artificial
<220> FEATURE:
<223> OTHER INFORMATION: primer s5020

<400> SEQUENCE: 16
ttaaggaatt tttctttagc cattctaaaa tcctccttaa gagg                      44
```

<210> SEQ ID NO 17
<211> LENGTH: 40
<212> TYPE: DNA
<213> ORGANISM: artificial
<220> FEATURE:
<223> OTHER INFORMATION: primer s5069

<400> SEQUENCE: 17
aaaaaagaat tcgatatcag atctacgcgt taacccgggc                          40

<210> SEQ ID NO 18
<211> LENGTH: 33
<212> TYPE: DNA
<213> ORGANISM: artificial
<220> FEATURE:
<223> OTHER INFORMATION: primer s5070

<400> SEQUENCE: 18
aaaaaacaat tgaatcgatt cacaaaaaat agg                                 33

<210> SEQ ID NO 19
<211> LENGTH: 30
<212> TYPE: DNA
<213> ORGANISM: artificial
<220> FEATURE:
<223> OTHER INFORMATION: primer s5071

<400> SEQUENCE: 19
aaaaaaagat ctcatggcag ggcttgagaa                                     30

<210> SEQ ID NO 20
<211> LENGTH: 33
<212> TYPE: DNA
<213> ORGANISM: artificial
<220> FEATURE:
<223> OTHER INFORMATION: primer s5072

<400> SEQUENCE: 20
aaaaaagaat tcttatttac ctctgtgctt ctt                                 33

<210> SEQ ID NO 21
<211> LENGTH: 21
<212> TYPE: DNA
<213> ORGANISM: artificial
<220> FEATURE:
<223> OTHER INFORMATION: primer s5097
<220> FEATURE:
<221> NAME/KEY: misc_feature
<222> LOCATION: (1)..(1)
<223> OTHER INFORMATION: Cy labeled

<400> SEQUENCE: 21
cactgtaccc tatctgcgaa a                                              21

<210> SEQ ID NO 22
<211> LENGTH: 23
<212> TYPE: DNA
<213> ORGANISM: artificial
<220> FEATURE:
<223> OTHER INFORMATION: primer s5098
<220> FEATURE:
<221> NAME/KEY: misc_feature
<223> OTHER INFORMATION: Cy labeled

<400> SEQUENCE: 22
attgagataa tcctcgatca ctt                                            23

<210> SEQ ID NO 23
<211> LENGTH: 30
<212> TYPE: DNA
<213> ORGANISM: artificial
<220> FEATURE:
<223> OTHER INFORMATION: primer s5139

<400> SEQUENCE: 23
aaaaaatgat cattacttgt acagctcgtc                              30

<210> SEQ ID NO 24
<211> LENGTH: 35
<212> TYPE: DNA
<213> ORGANISM: artificial
<220> FEATURE:
<223> OTHER INFORMATION: primer s5156

<400> SEQUENCE: 24
aaaaaatgat caccggtcga ttgccacatt aaagg                        35

<210> SEQ ID NO 25
<211> LENGTH: 19
<212> TYPE: DNA
<213> ORGANISM: artificial
<220> FEATURE:
<223> OTHER INFORMATION: primer s5203

<400> SEQUENCE: 25
gatatcctgc accatcgtc                                          19

<210> SEQ ID NO 26
<211> LENGTH: 21
<212> TYPE: DNA
<213> ORGANISM: artificial
<220> FEATURE:
<223> OTHER INFORMATION: primer s5208

<400> SEQUENCE: 26
ggtaccattt cttgctgaat a                                       21

<210> SEQ ID NO 27
<211> LENGTH: 26
<212> TYPE: DNA
<213> ORGANISM: artificial
<220> FEATURE:
<223> OTHER INFORMATION: primer s5209

<400> SEQUENCE: 27
cttaagcctg tcagtatcta cttgag                                  26

<210> SEQ ID NO 28
<211> LENGTH: 29
<212> TYPE: DNA
<213> ORGANISM: artificial
<220> FEATURE:
<223> OTHER INFORMATION: primer s5234

<400> SEQUENCE: 28
aaaaaaccgc tcgtcttcct aagcatcct                               29

<210> SEQ ID NO 29
<211> LENGTH: 31
<212> TYPE: DNA
<213> ORGANISM: artificial
<220> FEATURE:
<223> OTHER INFORMATION: primer s5235

```
<400> SEQUENCE: 29
aaaaaagaat tcgagatcag ggaatgagtt t                          31

<210> SEQ ID NO 30
<211> LENGTH: 44
<212> TYPE: DNA
<213> ORGANISM: artificial
<220> FEATURE:
<223> OTHER INFORMATION: primer s5236

<400> SEQUENCE: 30
ttaagaatta aaggaggaat tcaaaatggc agacaataac aaag            44

<210> SEQ ID NO 31
<211> LENGTH: 44
<212> TYPE: DNA
<213> ORGANISM: artificial
<220> FEATURE:
<223> OTHER INFORMATION: primer s5237

<400> SEQUENCE: 31
gatcctttgt tattgtctgc cattttgaat tcctccttta attc            44

<210> SEQ ID NO 32
<211> LENGTH: 42
<212> TYPE: DNA
<213> ORGANISM: artificial
<220> FEATURE:
<223> OTHER INFORMATION: primer s5262

<400> SEQUENCE: 32
aaaaaagcta gcgtttaaac aaaaagcgat tttaatgagc tg              42

<210> SEQ ID NO 33
<211> LENGTH: 31
<212> TYPE: DNA
<213> ORGANISM: artificial
<220> FEATURE:
<223> OTHER INFORMATION: primer s5362

<400> SEQUENCE: 33 ggtaccccccg ggtagcctgg atggatcaga a                         31

<210> SEQ ID NO 34
<211> LENGTH: 26
<212> TYPE: DNA
<213> ORGANISM: artificial
<220> FEATURE:
<223> OTHER INFORMATION: primer s5363

<400> SEQUENCE: 34
actagtgaat tccttttcca atcgca                                26

<210> SEQ ID NO 35
<211> LENGTH: 35
<212> TYPE: DNA
<213> ORGANISM: artificial
<220> FEATURE:
<223> OTHER INFORMATION: primer s5407

<400> SEQUENCE: 35
aaaaaaggcg ccgctagctg gagaatataa cggtt                      35

<210> SEQ ID NO 36
```

```
<211> LENGTH: 20
<212> TYPE: DNA
<213> ORGANISM: artificial
<220> FEATURE:
<223> OTHER INFORMATION: primer s5408

<400> SEQUENCE: 36
acactcctta agtctagaaa                                                    20

<210> SEQ ID NO 37
<211> LENGTH: 19
<212> TYPE: DNA
<213> ORGANISM: artificial
<220> FEATURE:
<223> OTHER INFORMATION: primer s5617

<400> SEQUENCE: 37
ggaggggaga aaacaccta                                                     19

<210> SEQ ID NO 38
<211> LENGTH: 32
<212> TYPE: DNA
<213> ORGANISM: artificial
<220> FEATURE:
<223> OTHER INFORMATION: primer s5618

<400> SEQUENCE: 38
aaaaaagata tctcaagaaa atcccccgct tt                                      32

<210> SEQ ID NO 39
<211> LENGTH: 42
<212> TYPE: DNA
<213> ORGANISM: artificial
<220> FEATURE:
<223> OTHER INFORMATION: primer s5932

<400> SEQUENCE: 39
aaaaaagcta gcgtttaaac agtataaaaa tcgctttttt cc                           42

<210> SEQ ID NO 40
<211> LENGTH: 38
<212> TYPE: DNA
<213> ORGANISM: artificial
<220> FEATURE:
<223> OTHER INFORMATION: primer s5933

<400> SEQUENCE: 40
aaaaaagcta gcgtttaaac cggaagcttc ggtaaaaa                                38

<210> SEQ ID NO 41
<211> LENGTH: 18
<212> TYPE: DNA
<213> ORGANISM: artificial
<220> FEATURE:
<223> OTHER INFORMATION: primer s5934

<400> SEQUENCE: 41
gtgcaggagc tcgttatc                                                      18

<210> SEQ ID NO 42
<211> LENGTH: 18
<212> TYPE: DNA
<213> ORGANISM: artificial
<220> FEATURE:
<223> OTHER INFORMATION: cre consensus sequence
<220> FEATURE:
<221> NAME/KEY: misc_feature
```

```
<222> LOCATION: (5)..(5)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 42
wwtgnaarcg nwwwcaww                                                18

<210> SEQ ID NO 43
<211> LENGTH: 50
<212> TYPE: DNA
<213> ORGANISM: Bacteriophage T7

<400> SEQUENCE: 43
cttaagaatt aaaggaggaa ttcaaaatgg cagacaataa caaaggatcc             50

<210> SEQ ID NO 44
<211> LENGTH: 89
<212> TYPE: DNA
<213> ORGANISM: artificial
<220> FEATURE:
<223> OTHER INFORMATION: sequence 5-3

<400> SEQUENCE: 44
aattgcgtcg agaccctgt gggtctcgtt ttttggatcc ccgggacgtc gagaccctg    60 tgggtctcgt tttttgttta aacaagctt                                    89

<210> SEQ ID NO 45
<211> LENGTH: 89
<212> TYPE: DNA
<213> ORGANISM: artificial
<220> FEATURE:
<223> OTHER INFORMATION: complementary to seq. id. No. 44

<400> SEQUENCE: 45
ttaacgcagc tctggggaca cccagagcaa aaaacctagg ggccctgcag ctctggggac  60
acccagagca aaaaacaaat ttgttcgaa                                    89
```